United States Patent [19]

Greene

[11] Patent Number: 4,863,258

[45] Date of Patent: Sep. 5, 1989

[54] APPARATUS AND STIMULUS DESIGN FOR PRODUCING AND EVALUATING BINOCULAR FIELD EFFECTS IN VISION

[76] Inventor: Ernest Greene, P.O. Box 413, Sun Valley, Calif. 91352

[21] Appl. No.: 902,436

[22] Filed: Aug. 29, 1986

[51] Int. Cl.⁴ .............................................. A61B 3/08
[52] U.S. Cl. ..................................... 351/201; 351/240
[58] Field of Search ............... 351/201, 240, 242, 237, 351/232, 233, 201, 202, 203

[56] References Cited

U.S. PATENT DOCUMENTS 2,196,906  4/1940  Sherman ............................ 351/201
2,294,382  9/1942  Burian ................................ 351/201

FOREIGN PATENT DOCUMENTS 2105057  3/1983  United Kingdom ................ 351/201

OTHER PUBLICATIONS

Dove, H. W. Ueber die Ursachen des Glanzes und de Irradiation . . . In (Poggendorff's) Annalen der Physik und Chemie, 1850, 169–189.
Helmholtz, H. von Handbuch der Physiologischen Optik, 1910, 417–430, translated by J. P. C. Southall, 1925, 512–528, Optical Society of America.
Levelt, W. J. M., On Binocular Rivalry, 1965, 55–63 (relevant section), Institute for Perception RVO-TNO, Soesterberg, The Netherlands.

Primary Examiner—Rodney B. Bovernick
Assistant Examiner—J. P. Ryan

[57] ABSTRACT

By using a viewing device and the proper configuration of visual stimulus material, one can create competition between the two eyes and determine what is perceived by a binocular observer. Where one eye sees light or pattern in a zone of the visual field, surrounded by a dark boundary, and the other eye sees stimulus material which does not have such a boundary, the material which is contained within the dark boundary will dominate the binocular perception. With some stimulus configurations the observer will see a bright, "lustrous" form which appears to float slightly above the stimulus surface. In other cases patterns presented to each eye will be dissected and combined into a composite perception which is determined by the presence of the dark boundary. Applications for the invention include testing of patients for impairment of vision and producing special effects in movies and other forms of entertainment.

19 Claims, 16 Drawing Sheets

BLACK

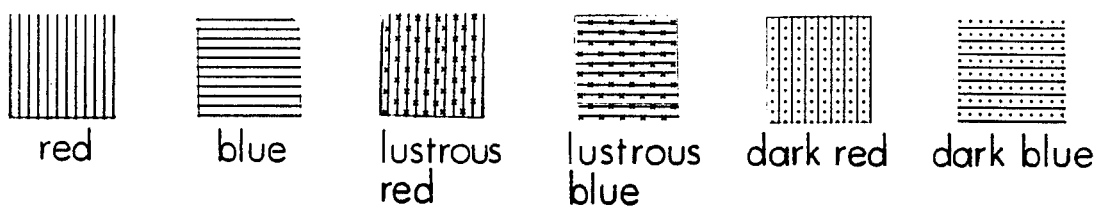
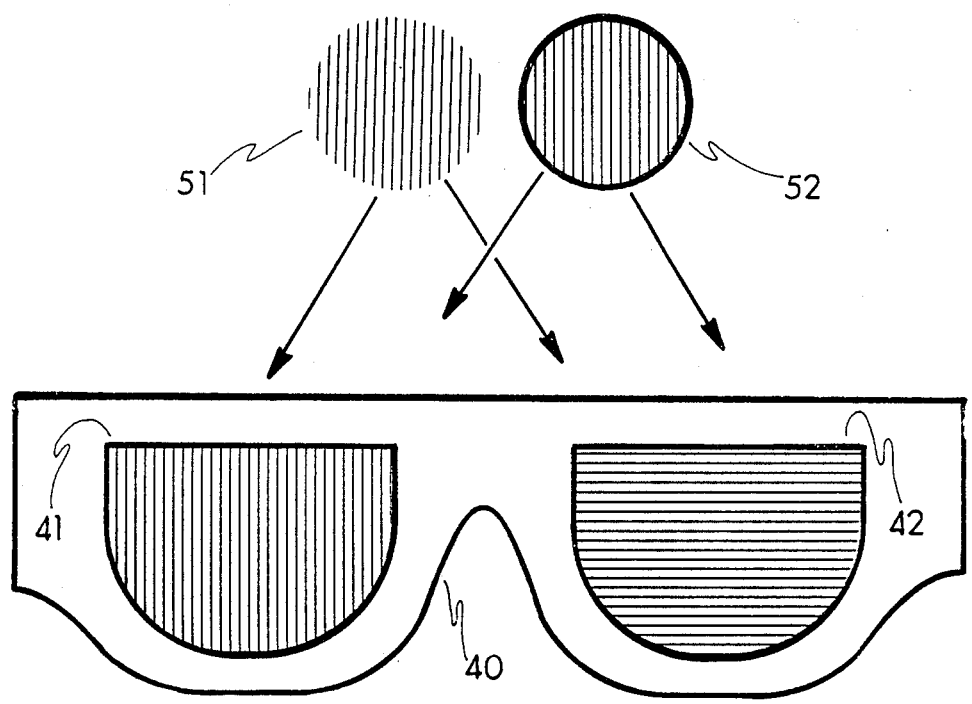
Fig 2A  Device and Stimulus
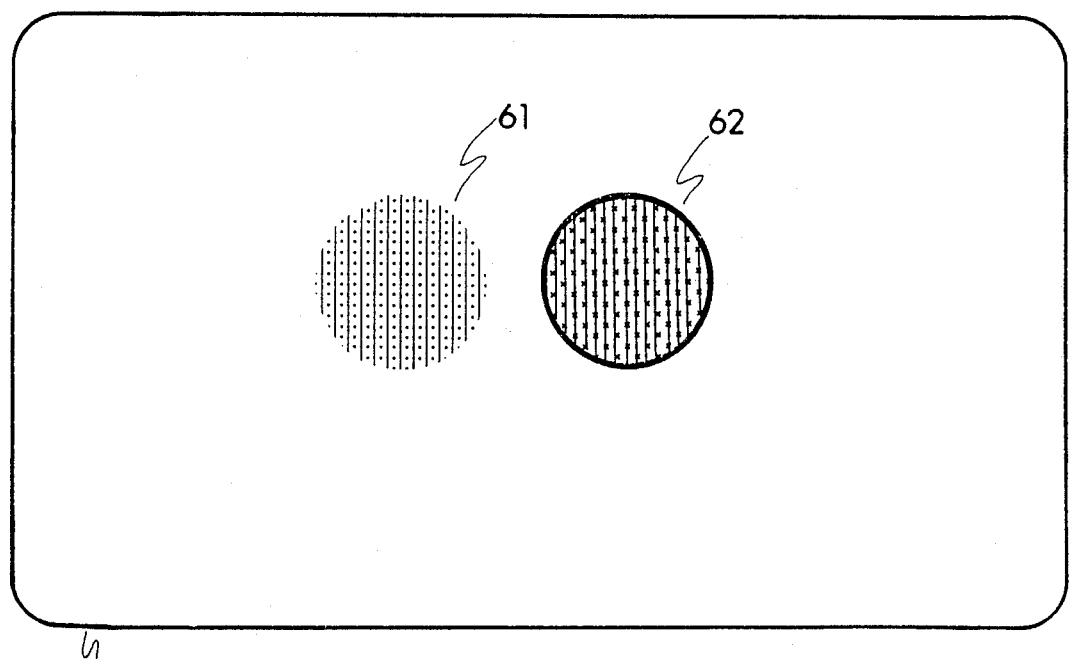
Fig 2B  Resulting Perception

APPARATUS AND STIMULUS DESIGN FOR PRODUCING AND EVALUATING BINOCULAR FIELD EFFECTS IN VISION

BACKGROUND

1. Field of Invention

The invention pertains to the field of visual perception, specifically to an arrangement for inducing certain novel and useful perceptions. These perceptions can create special visual effects for films, television, and other forms of entertainment. Also they can be used to evaluate visual dysfunction.

2. Background—Prior Art—FIGS. 1A–1C

It is known that when a human's two eyes see different images, it is possible to arrange the images so as to create a "competition" between the two eyes which can produce novel perceptual effects. In other words, if the two eyes send respective signals representing a pair of images to the visual centers of the brain, the visual centers will try to combine components parts of the two signals into a single perception. However, when the information contained by the images is incompatable, the visual center may selectively inhibit some of the information in forming the perception. This may be described as a "rivalry" between the eyes, though it should be understood that any synthesis or transformation of the information coming from each eye is accomplished by the brain.

FIG. 1A shows a prior-art visual set of images (called "stimuli" by Psychologists), comprising a black line drawing 11 of a multifaceted polygon with a white background surface, and a white line drawing 12 of the same polygon with a black background. These stimuli are paired to form stereoslide 10, which can be viewed stereoscopically to produce the perception of a single image which has a lustrous "gun-metal" surface. This is because the dark and light regions of the stimulus cause competition between the eyes (called binocular rivalry). This example of binocular rivalry was provided by H. von Helmholtz (*Handbuch der Physiologischen Optik*, 1910, plate IV-Q).

FIG. 1B shows a prior art stereoscopic slide 20 used by W. J. M. Levelt ("Binocular brightness averaging and contour information," *British Journal of Psychology*, 1965, pp. 1–13). This slide provides the right eye with a view of three black disks (22, 24, 26), while the left eye sees a hollow disk 21, a black disk 23, and a blank area 25 at the corresponding locations of the binocular visual field. When slide 20 is examined through a stereoscope, ring 21 is combined with disk 22, disk 23 is combined with disk 24, and blank area 25 is combined with disk 26. The perception which results is shown in Fig 1C; the viewer will perceive a bright disk at 31 and dark disks at 32 and 33. Using this stimulus configuration and these viewing requirements, Levelt was able to induce an increase in brightness in the immediate neighborhood of the stimulus contours, with the strength of the effect depending upon the size of the stimulus.

Observations by Helmholtz (op. cit.) and by those who preceded him had established that binocular conflict could produce the perception of luster, either when the images were presented by stereoscope or by viewing the objects through colored filters. However, none were accurate in establishing the essential conditions for producing the effect. H. W. Dove (*Poggendorffs Ann.* LXXXIII, 1850, p. 169) thought that differential refraction by the two eyes created depth cues which caused the images to be seen in different planes. This does not explain why the luster can be seen with black-and-white or monochromatic images. Helmholtz (op. cit., pp. 417–418) thought the luster was produced by a differential level of stimulation (i.e. a difference in brightness) at correponding points on the two eyes. When an observer with normal binocular vision fixates upon a real object, it provides the same brightness level to the corresponding point in each of the eyes. Under the unusual viewing conditions provided by the stereoscope, however, it is possible to provide the corresponding locations with different brightness levels, and Helmholtz thought this was the key factor in producing the perception of luster. As detailed below, the differential level of brightness is a factor in producing luster, but it is not the only factor. If it were, the binocular synthesis of disk 26 with blank area 25 would produce the perception of luster, since there is a brightness differential at corresponding locations of the two retina. In fact, this combination produces the perception of disk 33, which is seen as dark and having no luster. Levelt (op. cit.) described means by which contours would produce local control of brightness. His means included the centering of the stimulus within the field of view, because his analysis found that the local effects were strongest at the fovea. He stated that the strength of the brightness control was determined by the size of the stimulus, and his means for producing local control included the superimposition of the edges of the stimulus object presented to each eye.

OBJECTS AND ADVANTAGES

Accordingly, one principal object and advantage of the invention is to provide apparatus and means for inducing binocular rivalry (which controls perceptibility of brightness an pattern) by dark borders which are not limited to contours. Further, the apparatus and means induces this rivalry over a larger zone -- such that the perceptual effects are not restricted to the immediate neighborhood of the dark border. These large-scale influences will be referred to as "binocular field effects." Another object and advantage is to provide apparatus and means for inducing effects which are not restricted to foveal vision. A further object is to produce control of brightness where the edges of the images presented to the two eyes need not be coincident, and are not dependent upon the size or shape of the stimulus. The invention produces binocular rivalry using fewer elements than was heretofore available, and produces a greater diversity of effects—in particular, binocular field effects.

Still further objects are to produce special effects in films or with electronic images, to quantify the strength of the binocular field effect, so that abnormalities of vision may be tested, and to provide an optical device which measures the strength of binocular field effect, for use in research, instruction, and testing of adequacy of vision. Further objects and advantages will become apparent from a consideration of the ensuing description, taken in conjunction with the accompanying drawings.

BRIEF DESCRIPTION OF DRAWING FIGURES

FIG. 2A shows a viewing device and stimuli according to the invention for demonstrating luster; FIG. 2B and FIG. 2C illustrate the perceptual result, in which the disk with a black rim shows luster.

Drawing Reference Numbers

Figure 1A:
FIG. 1 (A & B) show examples of prior-art stimulus configurations which will produce the perception of luster.
FIG. 1C illustrates the perception from viewing FIG. 1B with a stereoscope.
Figure 1A:
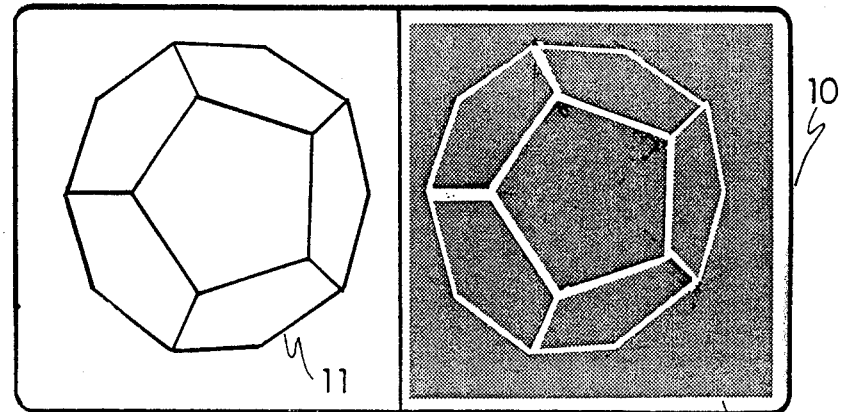
Figure 1B:
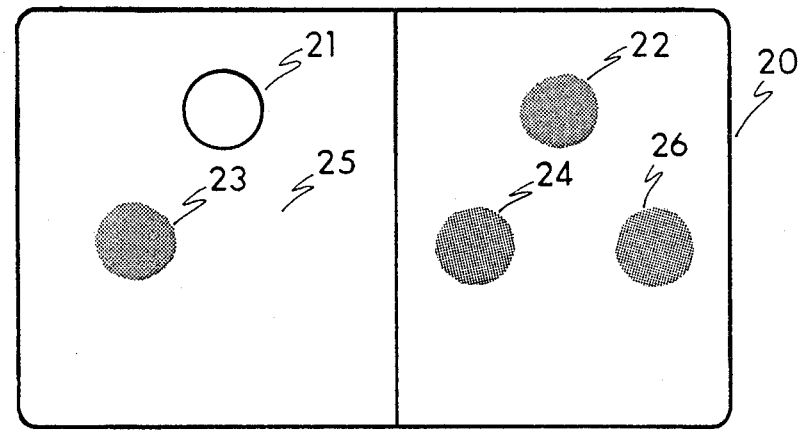
Figure 1C:
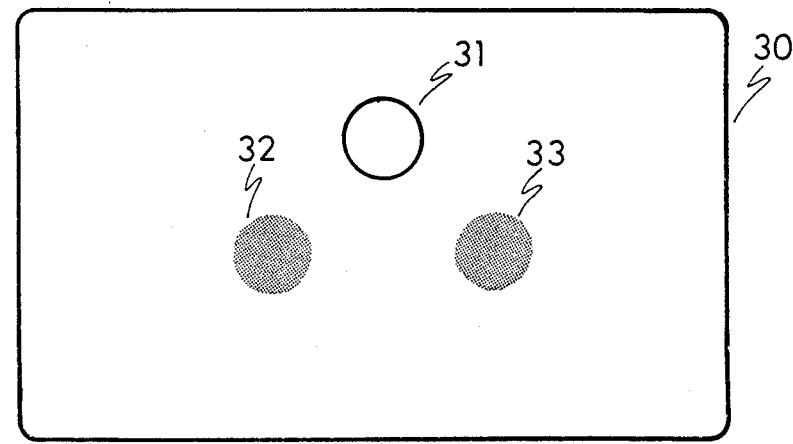

10 Helmholtz stereo slide
11 black drawing on white
12 white drawing on black
20 Levelt stereo slide
21 open ring (contour)
22 upper black disk, right eye
23 lower left black disk, left eye
24 lower left black disk, right eye
25 open space, left eye
26 lower right black disk, right eye
30 binocular perception from viewing 20
31 perceived upper disk showing luster
32 perceived lower left disk
33 perceived lower right disk
40 red-blue glasses
41 red filter
42 blue filter
51 red disk with no rim
52 red disk with black rim
60 binocular perception when viewing stimulus set 51 and 52
61 perceived ruddy red disk
62 perceived lustrous red disk
63 perception when viewing stimulus 51 and 52 through blue filter
64 perception when viewing stimulus 51 and 52 through red filter
70 fixation point
70' approximate edge of foveal zone
71 medium sized red disk/rim near fixation point 70
72 medium sized red disk/rim far from fixation point 70
73 small red disk/rim -continued 74 large red disk/rim
75 binocular perception from viewing stimulus set 71-74
76 perceived lustrous disk lying in foveal zone
77 perceived lustrous disk far from foveal zone
78 perceived small lustrous disk
79 perceived large lustrous disk
81 red crescent shape with rim
82 red star shape with rim
83 blue arrow shape with rim
84 blue heart shape with rim
85 binocular perception when viewing stimulus set 81-84
86 perceived lustrous red crescent
87 perceived lustrous red star
88 perceived lustrous blue arrow
89 perceived lustrous blue heart
90 hyperbolic red zone with one border
91 black line bordering 90
92 hyperbolic red zone with two borders
93 top border to 92
94 bottom border to 92
95 binocular perception when viewing stimulus set 90-94
96 perception of zone 90 as dark
97 perception of zone 92 as lustrous
101 red disk surrounded by squarish black form
102 blue disk surrounded by amorphous black form
103 adjacent red and blue half-disks surrounded by single rim
104 small blue disk inset within a red disk
105 red and blue checkerboard
110 perception when viewing stimulus set 101-105
111 perceived lustrous red disk within squarish black form
112 perceived lustrous blue disk within amorphous black form
113 perceived lustrous red and blue half-disks
114 perceived lusterous blue disk inset within lustrous red disk
115 perceived lustrous red and blue checkerboard
121 blue disk without black rim
122 blue disk with thin black rim
123 blue disk with medium black rim
124 blue disk with heavy black rim
125 perception when viewing stimulus set 121-124
126 perceived dark blue disk
127 perceived dark blue disk with rim of blue luster
128 perceived uniform blue lustrous disk
129 perceived uniform bright blue lustrous disk
131 hollow triangle with blue inset touching perimeter line
132 hollow triangle with blue inset not touching perimeter line
133 blue inset zone which touches 131
134 blue inset zone which does not touch 132
135 hollow square containing red checkerboard pattern
140 perception when viewing set 130
141 perceived triangle from viewing 131
142 perceived triangle from viewing 132
143 perceived lustrous blue inset
144 perceived dark blue inset
145 perceived checkerboard with most checks showing no luster
150 stereoslide with diagonal line patterns and circle
151 pattern stimulus for right eye
152 pattern stimulus for left eye
153 circular line superimposed on pattern 152
160 pattern perceived by binocular viewing of slide 150
160 pattern 151 is seen as the background, outside of circle
161 pattern 152 is seen as filling the circle
163 perceived circle controls perception of patterns 151 and 152
170 display of stimulus material in printed form
180 display of stimulus material by electronic device
190 projection device for display of stimulus material
191 viewing surface for display of stimulus material
250 stereoscope
260 stereoslide with stimuli configured to produce luster
270 left side of stereoslide
271 green mushroom shape with black rim
272 yellow arrow shape with rim
273 black disk
274 black rectangle
280 right side of stereoslide
281 black mushroom shape
282 black arrow shape
283 yellow disk with black rim
284 violet rectangle with black rim
290 binocular perception from viewing stereo slide 260
291 perceived lustrous green mushroom
292 perceived lustrous yellow arrow
293 perceived lustrous yellow disk -continued 294 perceived lustrous violet rectangle
300 device for projecting images with two polarities of light
301 light having a polarity different from 302
302 light having a polarity different from 301
305 image display screen
310 stimulus set with the two separate images overlayed
320 glasses which selectively filter two polarities of light
321 filter which passes only light 301
322 filter which passes only light 302
331 rimmed red disk with full luminance
332 rimmed red disk with some diminution of luminance
333 rimmed red disk with moderate diminution of luminance
334 rimmed red disk with greatly diminished luminance
335a unrimmed red disk - #1 of four comparison disks
335b unrimmed red disk - #2 of four comparison disks
335c unrimmed red disk - #3 of four comparison disks
335d unrimmed red disk - #4 of four comparison disks
340 binocular perception from viewing stimulus set 331-335d
341 perceived disk with bright luster
342 perceived disk with diminished luster
343 perceived disk with some luster
344 perceived disk with very little luster
345a perceived dark red disk from viewing 335a
345b perceived dark red disk from viewing 335b
345c perceived dark red disk from viewing 335c
345d perceived dark red disk from viewing 335d
350 stereo viewer for testing strength of field effect
360 front light source (hidden)
370 rear light source
400 slide composite for presenting perceptual stimulus
410 front component of 400 group, with stimulus examples
411 hole within the contour to allow rear illumination of zone
412 dark complement stimulus #1
413 dark complement stimulus #2
420 opaque mask to block light transmission from behind
421 hole in the mask to allow rear illumination of zone
430 polarized filter
500 rotatable polarized filter

Control of Luster—FIG. 2

FIG. 2A illustrates visual stimulus set 51–52, as well as viewing device 40 according to the invention which can be used to produce binocular field effects, including the perceptual experience of a bright, shimmering surface which may be described as "luster." Viewing device 40 is a pair of glasses containing, for the respective lenses, a set of color filters. These glasses provide the wearer with conflicting information about stimulus set 51–52. Viewing device 40 contains a red filter 41 in the left lens and a blue filter 42 in the right lens. For an individual of normal vision, these filters can be reversed without affecting the perception of luster.

Stimulus set 51–52 consists of two disks. Left disk 51 has no line or other border; it is red, as indicated by the vertical scoring. Right disk 52 is also red, and has a blackline border or rim. Disks 51 and 52 may be drawn on a white paper or projected upon a surface suitable for viewing.

When an observer of normal vision views disks 51 and 52 through glasses 40, the resulting perception is shown in Fig 2B. Disk 51 will be perceived as dark disk 61, and disk 52 will be perceived as lustrous disk 62. Lustrous disk 62 is seen as having a shimmering, color-saturated quality, as indicated by the crosses in the illustration, and will appear to float slightly above the page.

Figure 2C:
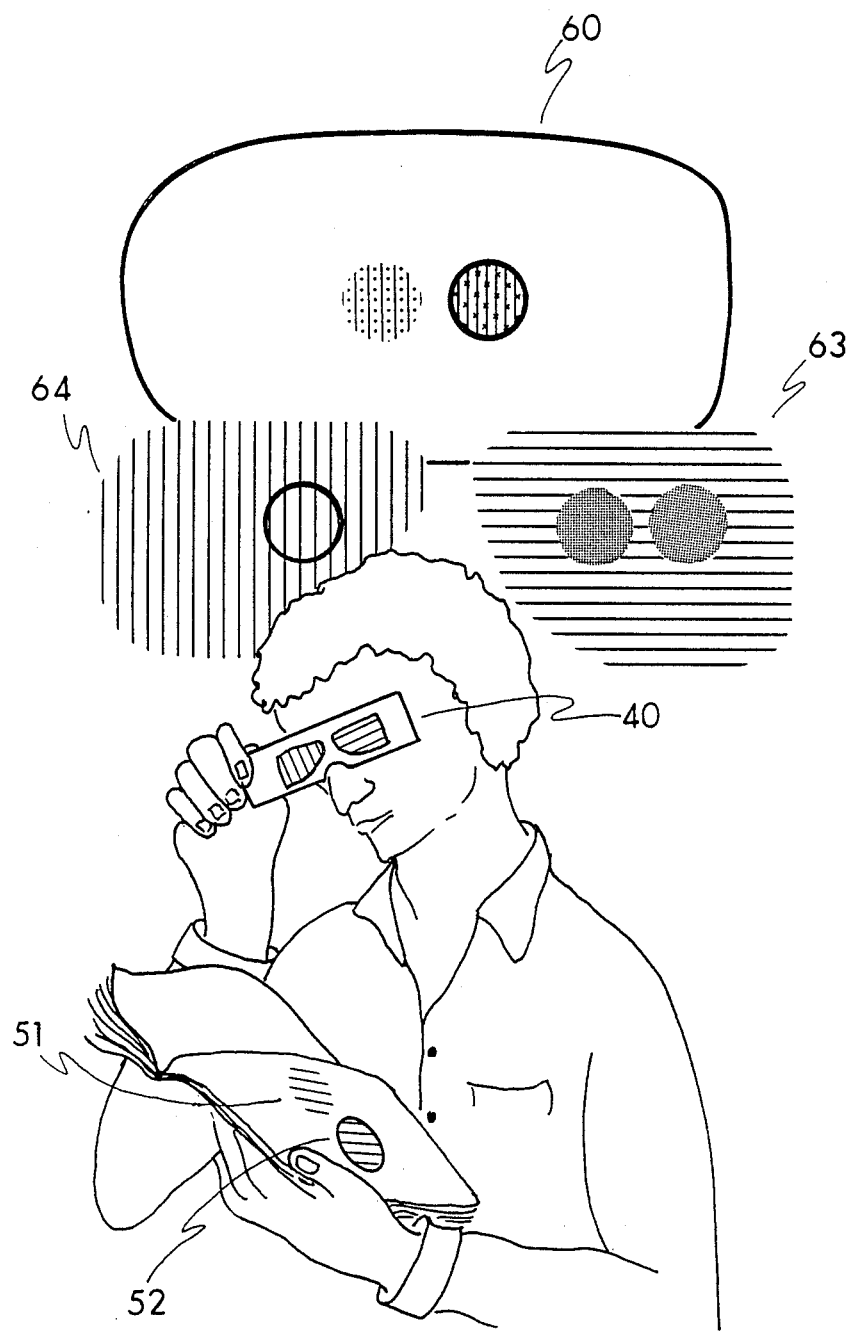

This perceptual phenomenon is created because the color filters segregate the image components to the viewer's respective eyes. FIG. 2C illustrates the stimuli and viewing conditions described above, and provides additional detail about the how the glasses provide conflicting information to each of the observer's two eyes. (Note that optical inversions are not reflected by the illustration, and except for the monocular views, the image components are the same as shown in FIG. 2A and 2B.) Through the blue filter, the eye registers image 63, and image 64 is registered through the red filter. In image 63, disk 51 is seen as a dark, virtually black solid disk. Disk 51 cannot be seen through the red filter (in image 64), and so that location is filled with "background" light. The binocular synthesis of the image components from the two eyes results in the perception of a dark, ruddy red disk 61.

As seen through the blue filter (in image 63), disk 52 also is registered as a dark, virtually black disk. However, in image 64 the eye registers disk 52 as a hollow ring, filled inside and outside with bright red color. The perception of the dark boundary line controls and determines the synthesis of information from the two eyes, so that the stimulus material lying inside the boundary (the bright red light) dominates perception. Thus the binocular perception of disk 52, when viewed through glasses 40 will be of a bright, lustrous disk 62. The dark disk being registered upon one eye through the blue filter is inhibited, and will not be perceived by the observer. (Direct demonstration of these perceptual effects are provided in my paper, "Form Light, Form Bright," *Neuropsychology Foundation Monographs,* 1985, 2–11).

The system in FIG. 2 differs from the demonstrations of Helmholtz and Dove (op. cit.), did not delineate the contribution of a dark perimeter in producing binocular rivalry. It differs from the work of Levelt (op. cit.) in several ways. Levelt stated that a contour would affect the way light is combined at two corresponding parts of the retina. He stated that in the absence of a contour, the two eyes would average the amount of light from corresponding zones, but that a contour would tip the balance, causing the brightness from one eye to dominate the average. He suggested that the influence of the contour was a function of distance -- the dominance of the eye seeing the contour would be less at points lying at a distance from the the contour. In a separate work (*On Binocular Rivalry,* Institute for Perception RVO-TNO, 1965, pp. 56–57), Levelt states even more explicitly that the strength of the effect is dependent upon the "size of the disk" (the area contained by the contour). In an article entitled "Some demonstrations of the complementary functioning of the eyes," *Perception & Psychophysics,* 1966, pp. 39–40) he states: ". .the smaller the distance d between the fixation point of an eye and a monocular contour in the field of this eye, the more the weighting coefficient of this eye tends to unity in the point of fixation." Thus Levelt proposed that there is a gradient in the retina, such that a contour has more influence when it is seen by the fovea (in the vicinity of the fixation point) than when it is seen by the edge of the eye.

The present invention provides apparatus and means for achieving nonlocal binocular rivalry, also called "binocular field effects." The stimulus configurations needed to produce these perceptual phenomenon were not available or described until the appearance of my monograph "Form Light, Form Bright," (op. cit.). Further, the range of perceptual effects which are provided by these means is much greater than has been demonstrated for any other form of binocular rivalry. Below, a number of demonstrations are given, with special emphasis on the range and diversity of perceptions which are possible using means which are not limited by local control processes.

Figure 3:
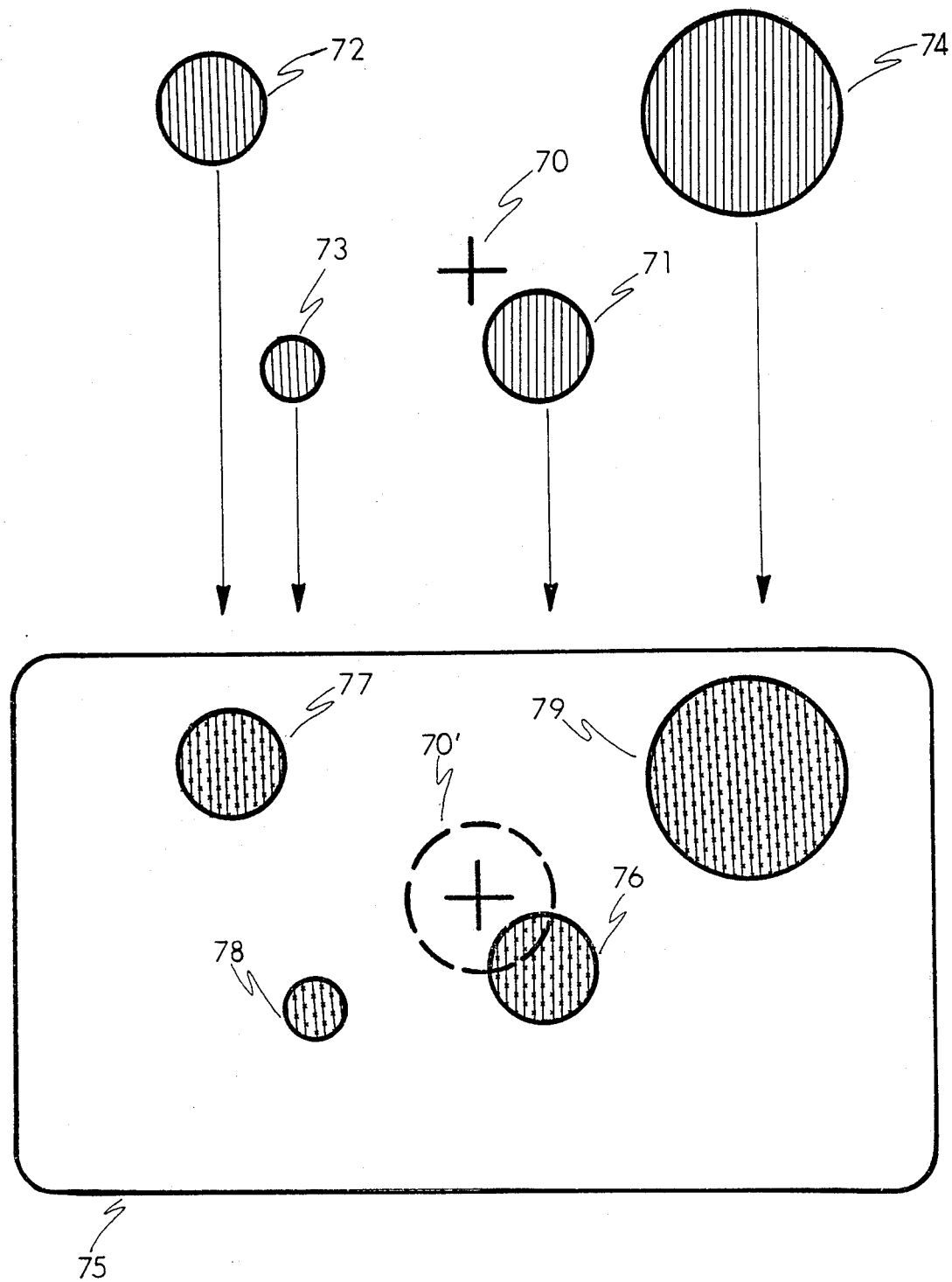
FIG. 3 shows that stimuli which vary in size and position in the visual field will have uniform luster.

Stimulus Size and Location Is Not Critical—FIG. 3

The figure shows a stimulus set 71-74, which consists of a plurality of red disks which vary in size and location from a fixation point 70. An observer who views this stimulus collection through red-blue glasses 40 (FIG. 2A), and who looks at fixation point 70 will perceive the forms shown as binocular perception 75. Broken ring 70' shows the approximate boundary of the area seen by the fovea. Perceived disk 76 lies partly within the fovea, so that some parts of the disk are near the center of the fovea and some parts are farther away. This configuration is able to produce binocular field effects, i.e., a broad control of the zone contained by the dark border. In this example, disk 76 will appear a uniform, lustrous red. Similarly, perceived disk 77 will appear as bright as disk 76, even though it lies at a great distance from the fovea. Perceived disk 79 will appear a uniform, lustrous red across the entire surface of the disk, even though the central zones of the disk lie farther from the dark perimeter line than those near the edge. In fact, disks 76-79 will appear uniform and equal in luster irrespective of their size or position in the visual field.

Figure 4:
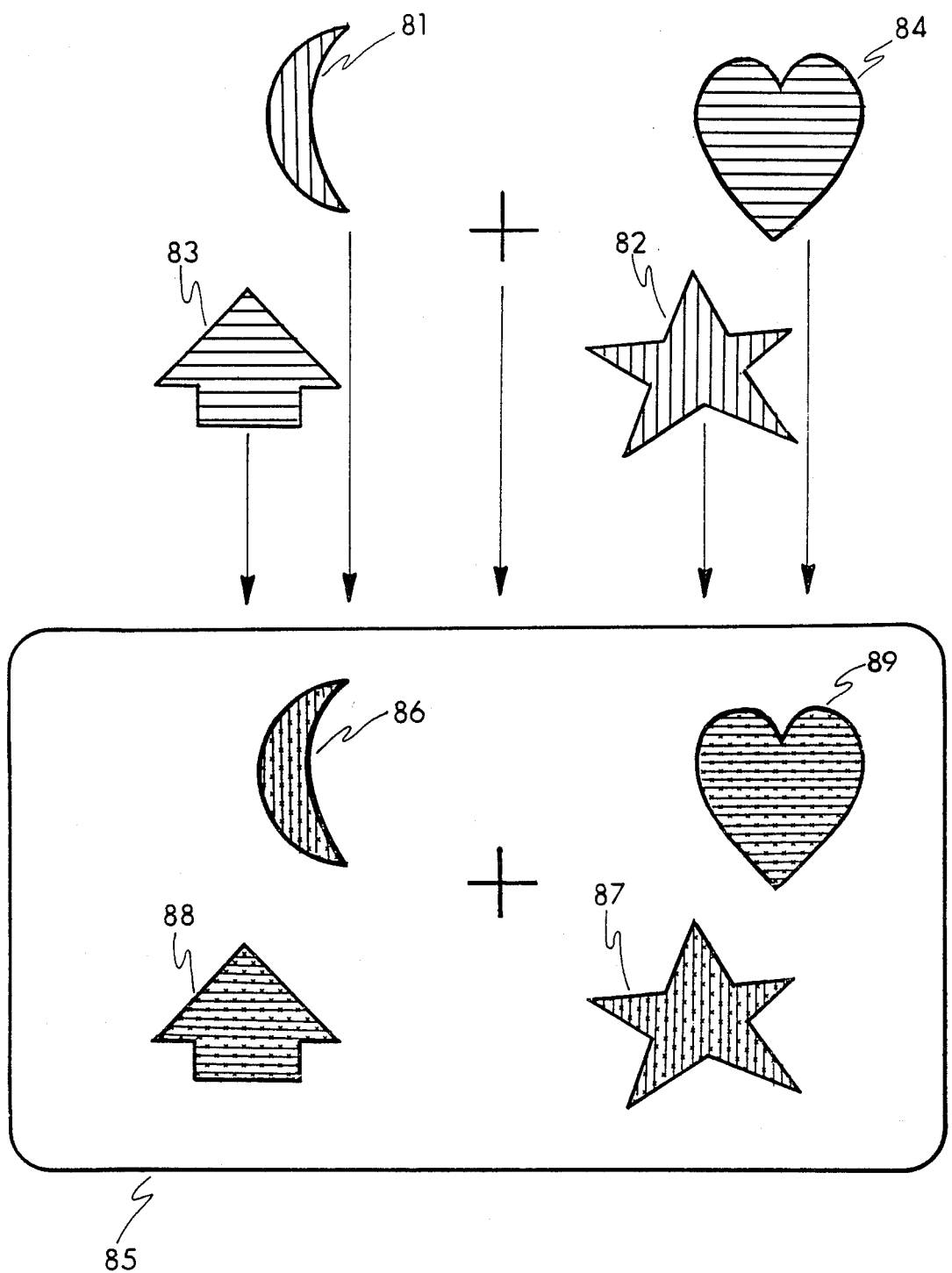
FIG. 4 shows various shapes with uniform luster, and shows that colors presented to opposite eyes can produce luster simultaneously.

Shape Not Critical—FIG. 4

Binocular field effects are able to act at a substantial distance from the border which controls the process. Because of this, the strength of the effect does not depend upon the proximity of the border to the various zones within the form. FIG. 4 shows stimulus set 81-84, consisting of four forms (crescent 81, star 82, arrow 83 and heart 84) which are colored either red (vertical lining) or blue (horizontal lining) and are bordered by a black line. When viewed with red-blue glasses 40 (FIG. 2) they produce binocular perception 85. Red crescent 86 will exhibit the same amount of luster as red star 87, and the luster will be uniform across the surface of each shape. Similarly, blue arrow 88 will exhibit the same amount of luster as blue heart 89, and again the luster will be uniform.

Simultaneous Luster of Red and Blue—FIG. 4

Binocular rivalry is often explained as the domination of one eye over the other. This explanation is inconsistent with the fact that one will be able to perceive red and blue luster simultaneously, as is the case for the stimulus group shown in FIG. 4. The conditions for producing red luster would require that the eye looking through filter 41 would have to dominate perception, and for blue luster to be seen the eye looking through filter 42 would have to be dominant. Since both lustrous colors are seen at the same time, the demonstration shows that binocular field effects can be controlled simultaneously by the appropriate presentation of stimulus elements to the two eyes.

Figure 5:
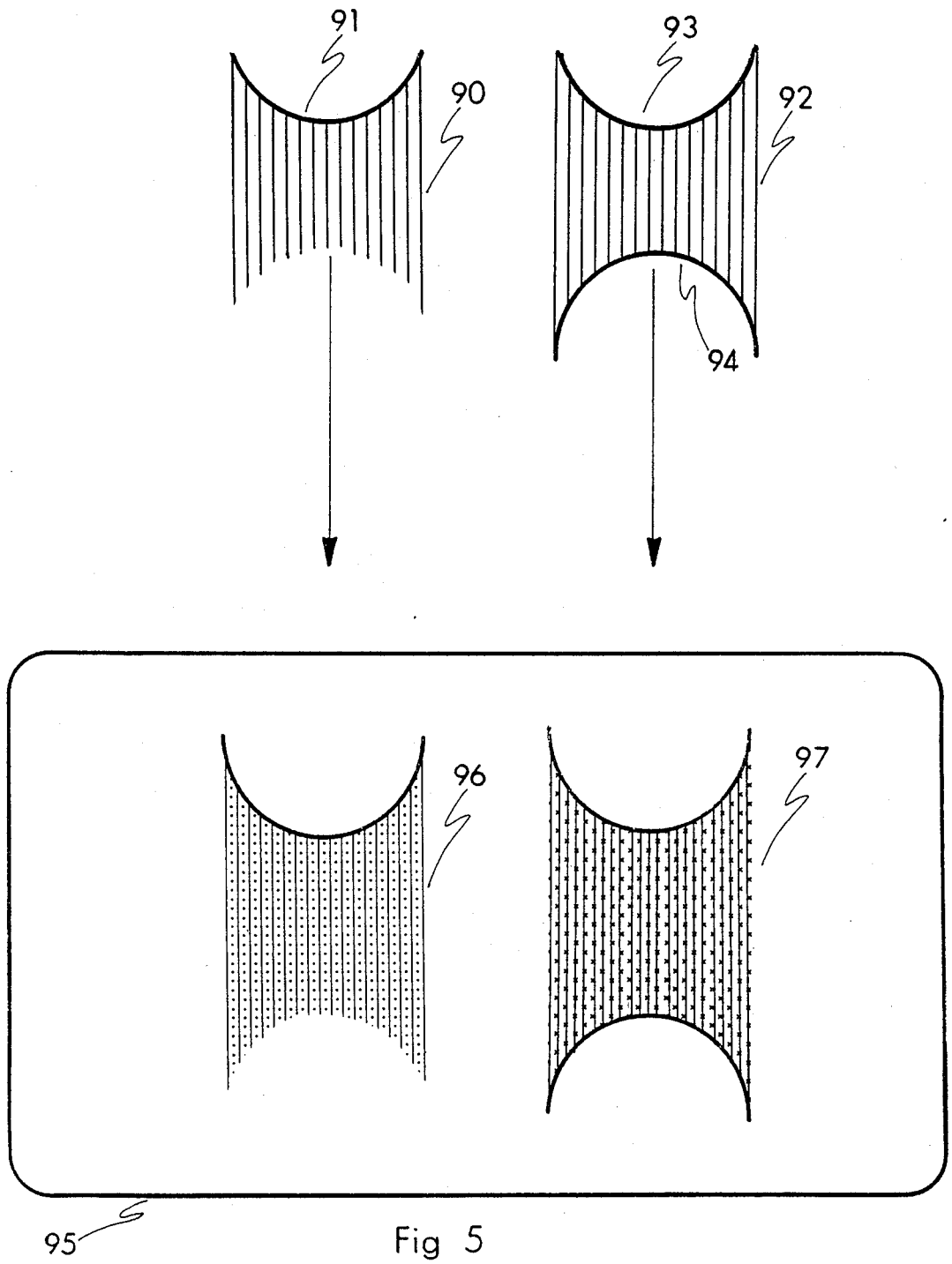
FIG. 5 shows geometric figures which are bordered by contours, and that certain contours will not induce luster.

The Importance of Containment—FIG. 5

Containment by dark border is an essential element in control of binocular field effects. This is illustrated in Fib 5, where a red hyperbolic 90 (which is partially bounded by contour 91) will not be perceived as having luster even when the stimulus material is positioned so that it falls on the fovea of the eye. As shown at perception field 95, this stimulus will be perceived as a dark, somewhat ruddy-red form 96. Luster will be seen only when the stimulus contours operate to "contain the zone," as is true with contours 93 and 94, which provide containment of hyperbolic shape 92. The field effects produced by these perimeter elements results in the perception of the lustrous hyperbolic shape 97. In general, the amount of luster produced by a dark boundary is a direct function of the extent of containment. Broken or partial boundary lines will have proportionately less influence than will a solid line.

Figure 6:
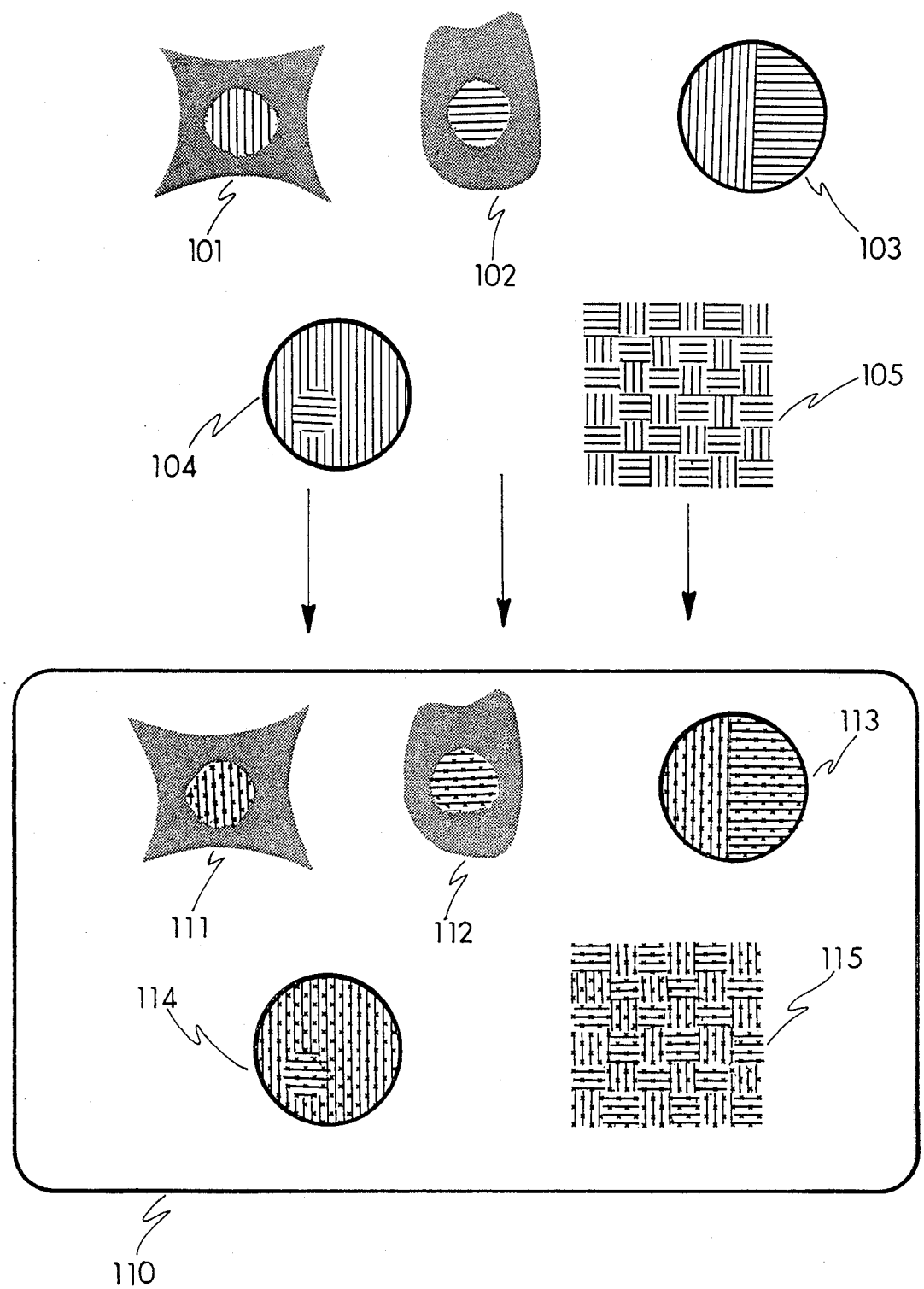
FIG. 6 shows that a dark boundary edges can produce luster, and that one color can provide such an edge for another.

Black Edges Work Like Contours—FIG. 6

FIG. 6 contains a stimulus set 101-105, which when viewed with glasses 40 (FIG. 2) will be seen as binocular perception 110. Stimulus 101 is a red disk surrounded by a squarish black form, and stimulus 102 is a blue disk surrounded by an amorphous black form. The resulting perception will be lustrous red and blue disks, respectively, as shown in perceived forms 111 and 112. This demonstrates that the boundary of the disk need not be a contour, but can be a dark zone of indefinite dimensions.

Note also that the edge of the form seen by each eye need not be coincident. The red-filtered eye sees a small bright circle surrounded by an amorphous dark form. To the blue-filtered eye the amorphous form appears completely dark -- one does not see any rim at the location which corresponds to the border of the disk seen by the other eye. Thus the control of luster does not depend upon presentation of coincident edges to the two eyes.

The perimeter may contain more than one color, as shown with disk 103 which contains red and blue half-disks, and disk 104 which has a small blue disk set within a larger red disk. When viewed through glasses 40, these disks will show luster, as illustrated with perceived disks 113 and 114. This occurs because each color appears black when it is viewed through the opposite filter—41 or 42 (FIG. 2). The dark appearance of the color provides a "functional boundary" for the color zone which it contains.

As an additional example, red and blue checkerboard 105 contains no black, yet it will appear lustrous as shown by perceived checkerboard 115. The view through red filter 41 provides a perception of red checks surrounded by black checks, the adjacent checks (as seen through the red filter) providing a dark boundary for the red zones they contain. The converse applies to the view through blue filter 42.

Figure 7:
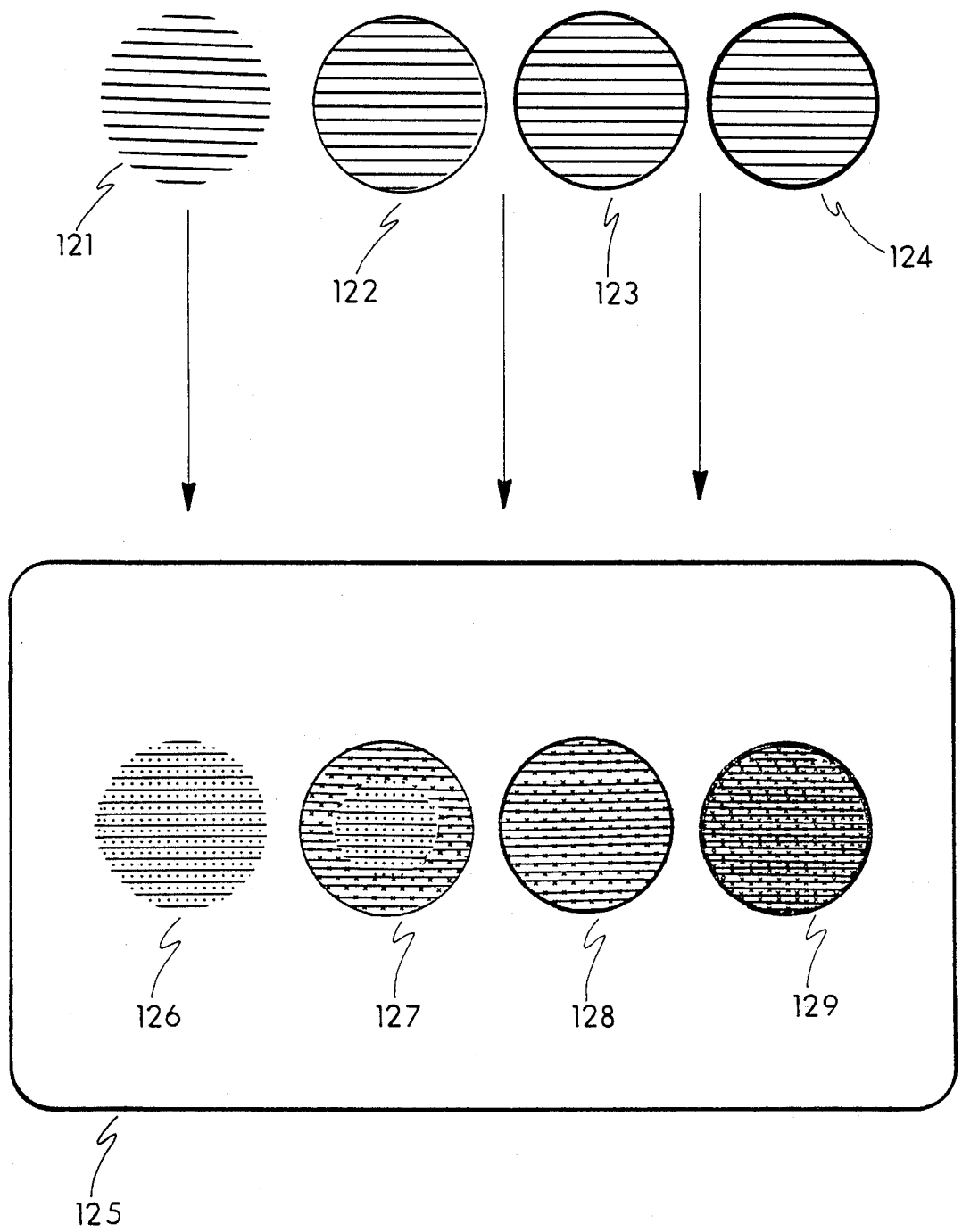
FIG. 7 shows a number of disks which differ in thickness of the perimeter rim; the thickness of the rim determines the level of luster.

Line Thickness in Amount of Luster—FIG. 7

The thickness of a perimeter rim can be a factor in the strength of effect. FIG. 7 shows a disk array 121-124 which has individual blue disks whose perimeter lines increase in thickness. Disk 121 does not have a dark boundary line. If this disk is viewed with glasses 40 (FIG. 2) it appears a dark blue-black, with no luster as shown in perceived field 125 at disk 126.

The thin line used for disk 122 induces a slight amount of luster, as shown by perceived disk 127 which is seen as a dark disk surrounded by a bright blue ring just inside the perimeter line. With thicker lines, the luster grows stronger and becomes uniform across the entire disk.

For disks 123 and 124 (medium and thick rims) the luster will look progressively brighter as a function of the thickness of the black rim (but it appears uniform across the surface for each of the disks). At about this thickness a maximum is reached, and the rim can be indefinitely thick (filling the remainder of the visual field) and the luster will not get any brighter.

Figure 8:
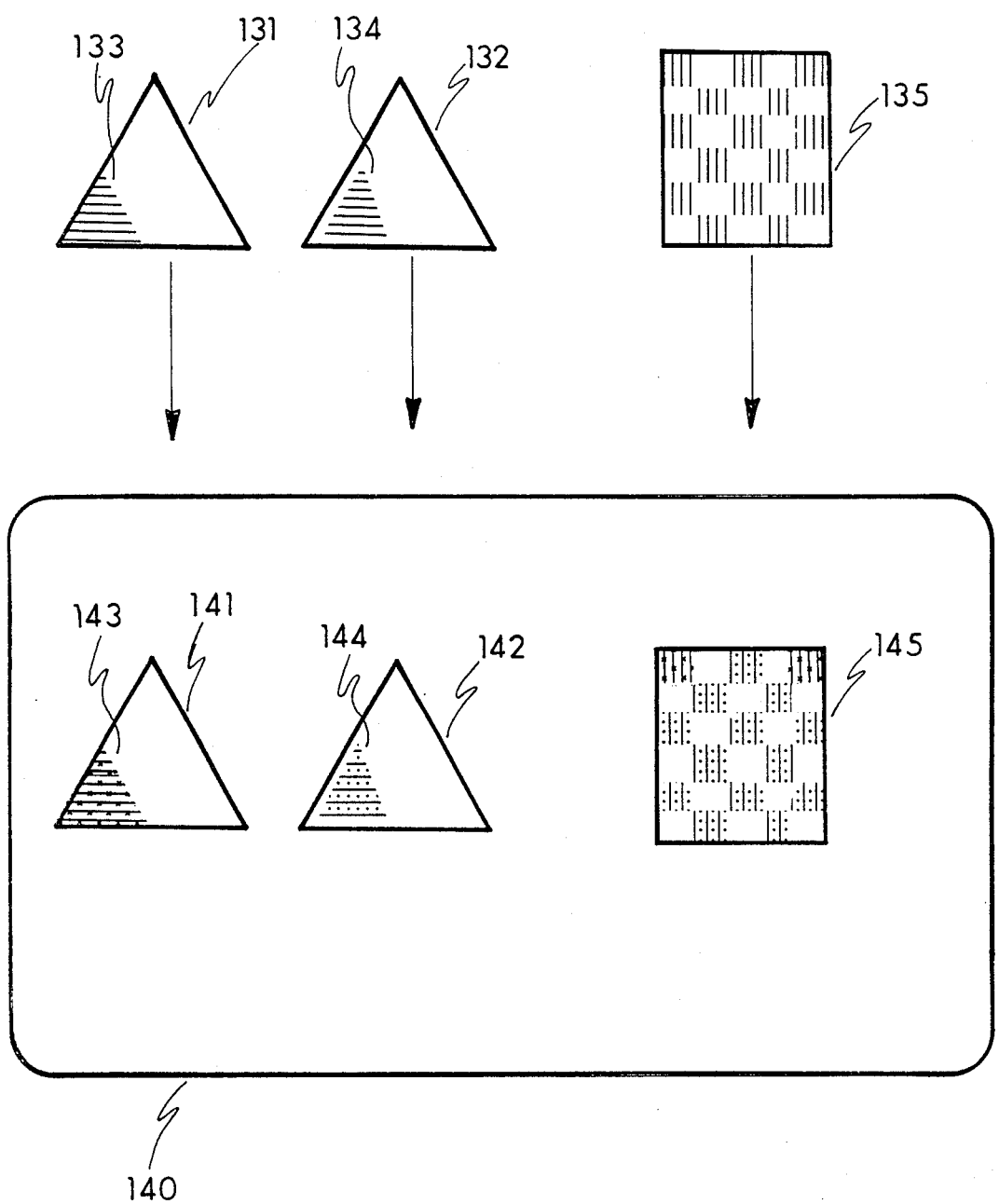
FIG. 8 shows a number of stimuli which vary in the degree of direct contact between the color zone and the dark boundary; amount of direct contact determines the amount of luster.

Contact with the Dark Border—FIG. 8

An additional important factor is the size and continuity of color mass as it relates to direct contact of the functional border. Little or no luster will be produced if the color is broken into small zones, or otherwise fails to make contact with the dark border. In FIG. 8, stimulus set 131-132 (consisting of triangles with blue inserts) will be perceived as triangles 141 and 142 (part of binocular perception 140) when they are viewed with glasses 40 (FIG. 2). Triangle 131 contains a blue insert 133, which is contiguous with the perimeter line. Insert 133 will appear lustrous, as shown at 143 in perception field 140. However, blue insert 134 is not contiguous with the perimeter of triangle 132. As a result, perceived insert 144 will be seen as dark blue-black in color and having no luster.

Most of the red squares in checkerboard 135 do not make contact with the perimeter line, and thus the squares in perceived checkerboard 145 show no luster. The corner squares which make contact with the perimeter on two sides will show some luster. The lack of luster in this case should be contrasted with the luster which is seen in perceived checkerboard 115 (FIG. 6), where there are red and blue squares which can provide functional borders for each other.

Contrast of Contained Zone

Luster is greatest when there is extreme contrast in what is perceived in the zone by the two eyes. This is exactly the opposite of Helmholtz' theory (op. cit.). He proposed that perception of a lustrous surface was due to a differential of brightness or color as seen by the respective eyes, but further specified that the effect would be strongest where the difference was not very great. In fact, it can be shown that the most luster is seen when one eye perceives bright light in the zone contained by the dark border, and the other sees total blackness at that site.

Depth Element is Not Based on Binocular Disparity

The perception of depth in the image (with the colored form floating slightly above the surface) is not due to binocular disparity in the image. Binocular disparity cues are provided by slight misalignment of the images which are presented to the respective eyes. This is the principle behind the use of stereoscopes and twin-image projection using polarized light (so called "3-D movies") to enhance perception of depth. In the present case there is no misalignment of image components which can produce any disparity. Instead, the current phenomenon is based on a "binocular field effect" to establish the dominance of certain components in the image, and additionally the viewer attributes depth (floating) to the perceived form.

Summary of Luster Control

Accordingly, I have found that various viewing conditions and stimulus configurations will produce the perception of luster. The phenomenon may be seen by an observer who has a normal balance of binocular vision, when two basic conditions are met:
(a) the images presented to the respective eyes have regions which differ substantially at corresponding locations in each eye (i.e. one eye seeing bright light and the other seeing darkness at the same location)
(b) the eye which sees the zone of bright light also sees that zone as being surrounded by a dark border The strength of the luster effect is determined by:
(1) the degree to which the zone is contained or bounded all around by the dark border,
(2) the magnitude of the brightness difference between the two eyes at the location of the dark-bordered zone,
(3) the thickness of the line or other stimulus material which forms the border, and
(4) the presence of direct contact between stimuli having a brightness differential between the two eyes, and the dark border which surrounds the zone containing these stimuli.

Variations in stimulus elements listed above have a role in determining what is perceived, and can be manipulated systematically as a method to control the strength of the perceptual effect. As discussed previously, for a person of normal binocular vision, the location, size, and shape of the bounded zone are not important as factors in determining the strength and uniformity of the luster effects nor is it necessary to have corresponding positioning of the edges presented to the two eyes.

Figure 9:
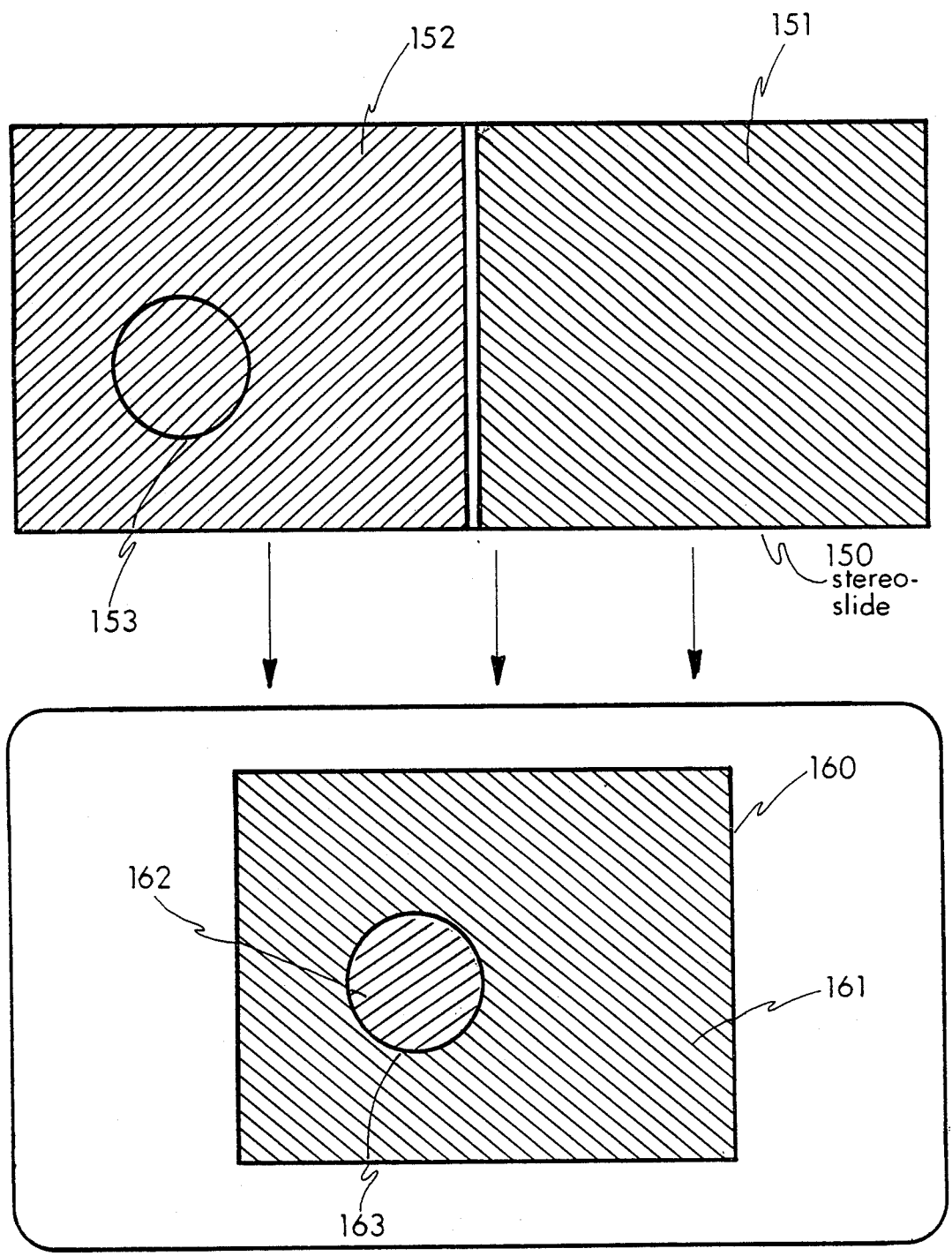
FIG. 9 shows a stereo slide which presents the two eyes with line patterns which differ in tilt, and also presents one eye with a hollow ring; the ring determines which is perceived in the zones inside and outside the ring.

Control of Pattern—FIG. 9

It is also important to note that the binocular field effects are not the exclusive province of brightness or color. Perceptions of patterns (colored and non-colored) can be determined by the binocular field effects. For example, FIG. 9 shows a stereoslide 150 which can be presented to the two eyes using a stereo viewer, polarized light projector, or a related procedure (stereo viewer not shown). Note that the lines shown in the illustration are meant to portray the actual lines of the stimulus—color is not represented in this particular case.

The right eye sees diagonal lines 151 and the left eye sees lines 152. The left eye also sees a hollow ring 153.

Binocular perception 160 contains elements from each of the eyes. The viewer will perceive a ring 163, and the perception of this ring will determine what is seen inside and outside the zone contained by the ring. Perceived pattern 162 inside the ring is perceptually derived from pattern 152 (which is presented to the same eye that sees ring 153). Perceived pattern 161 outside the ring is perceptually derived from pattern 151. This pattern was presented to the right eye, which is not provided with a view of ring 153. Thus, perception in the zones inside and outside perceived ring 153 are determined by the selective presentation of the stimulus ring to one eye but not the other.

Stimulus Design Depends on Viewing Apparatus

The design of the pattern for showing binocular field effects will depend somewhat on the method of segregation of the images. If a stereoscope is used, the stimulus slide will look approximately like that of FIG. 9, and the lines of the stimulus, as well as the background can be in black and white, or any color combination.

The resulting perception will be a composite in which the lines and background color are segregated according to whether they fall inside or outside the zone contained by the perimeter line. Mixing of line and color elements from the two images is minimal.

If the stimuli are projected upon a screen using polarized light, then patterns 151 and 152 (as well as ring 153) will be separated on the film which is used to make the projection, but the images will be superimposed upon the screen, and then resegregated by the use of polarized filters placed in front of the two eyes like glasses.

If the segregation of images is to be accomplished with colored filters, as with glasses 40 (FIG. 2), then patterns 151 and 152 (as well as ring 153) must be drawn superimposed, and in color—e.g. with pattern 151 drawn using red lines, and pattern 152 and ring 153 drawn using blue lines. The red lines will appear black when they are viewed through blue filter 42 (FIG. 2), and they cannot be seen through red filter 41 (FIG. 2). Conversely, the blue lines will be seen as black when viewed through the red filter (41), but cannot be seen through the blue filter 42. The combined perception 160 will be approximately black and white, and the effect of the perceived perimeter in inducing binocular field effects is manifested by the selective perception of one pattern inside the perimeter, and the other pattern outside the perimeter.

This particular effect depends on a relatively even balance of overall pattern-strength, and the effect is strongest where the rivalrous patterns would be seen as a patch-work quilt were it not for the presence of the hollow ring.

Zonal Control of Binocular Field Effects

It should be clear that the invention is a specification of the devices and stimulus conditions for producing zonal control of binocular field effects. By the selective presentation of separate images to the two eyes, it is possible to provide one eye and not the other with stimulus material which allow it to dominate the competition between the eyes and to determine the final perception. In particular, where one eye sees a dark boundary and the other does not, the observer will generally perceive whatever material is contained by that boundary, as seen by the eye which is able to see the boundary.

The brightness enhancement (i.e. luster) phenomenon represents a special case of the more general effect. If stimulus material is presented in black and white, then a dark border seen by one eye will create an enhancement of brightness in the zone contained by the perimeter. If that area has color which can be seen by the eye which sees the perimeter, then the color will be seen as being saturated and having a lustrous glow. If that zone is filled with a pattern—lines, dots, or whatever, then the perception inside the perimeter will be of that pattern, and patterned material from the other eye will be inhibited.

It should be clear, therefore, that the factors which determine the strength of luster also determine the control of pattern perception. Thickness of the perimeter line, the degree to which it "contains" a given zone, the relative balance of material in the respective eyes, and the contiguity of material within the zone and the boundary are all factors in determining the strength of effect. While they are specified most completely with respect to luster, it should be clear that they apply also in relation to perception of patterns.

Alternative Methods of Stimulus Display—FIG. 10

Figure 10A:
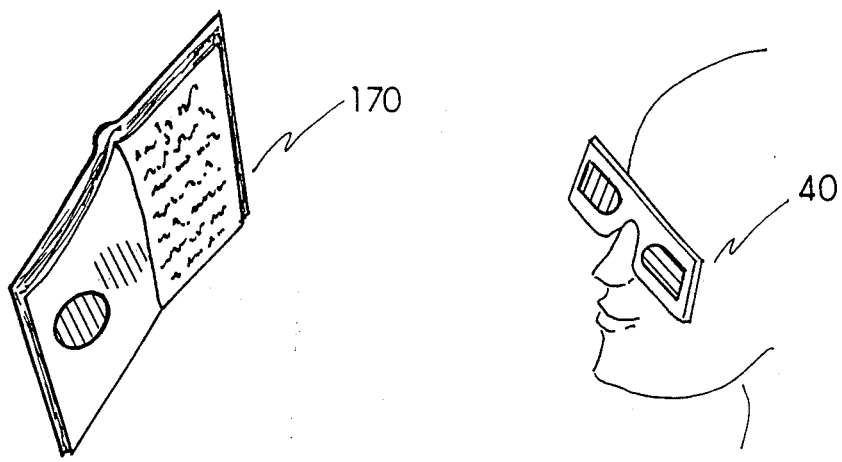
FIG. 10 (A to C) illustrates methods for presenting stimulus materials so that luster may be perceived.

The medium which is used to present an image is not critical, so long as the perceptual relationships described above are preserved. As illustrated in FIG. 10A, the stimulus elements can be printed on a page or any other suitable viewing surface 170. Any method of pigmentation of the surface, such as photographic printing, lithography, or xerography, can provide suitable stimulus elements. Likewise, the stimulus elements can be hand-drawn or constructed by lamination or other method of fabrication.

Figure 10B:
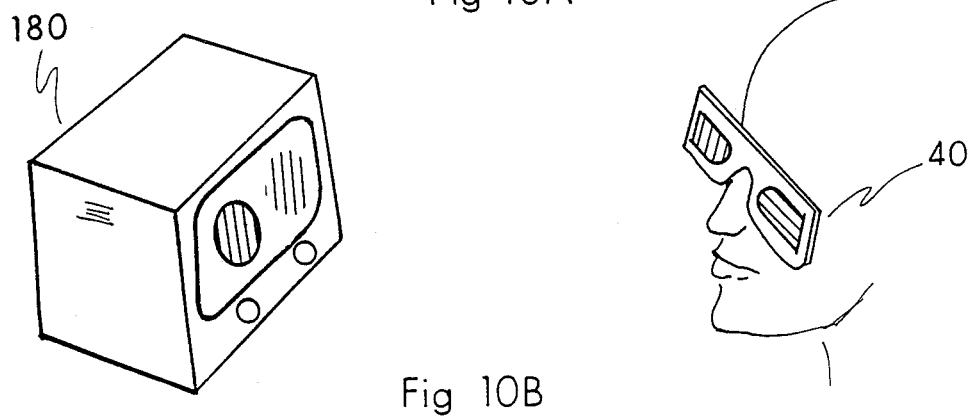

FIG. 10B shows the stimulus elements being presented on an electronic device 180. This might correspond to a standard television or computer monitor, but would also include other methods of electronic display, such as a liquid crystal display, light-emitting diode array, a plasma display or other device designed to provide a viewable image. Although a still frame is illustrated, the perceptual effects can be produced with moving images as well.

Figure 10C:
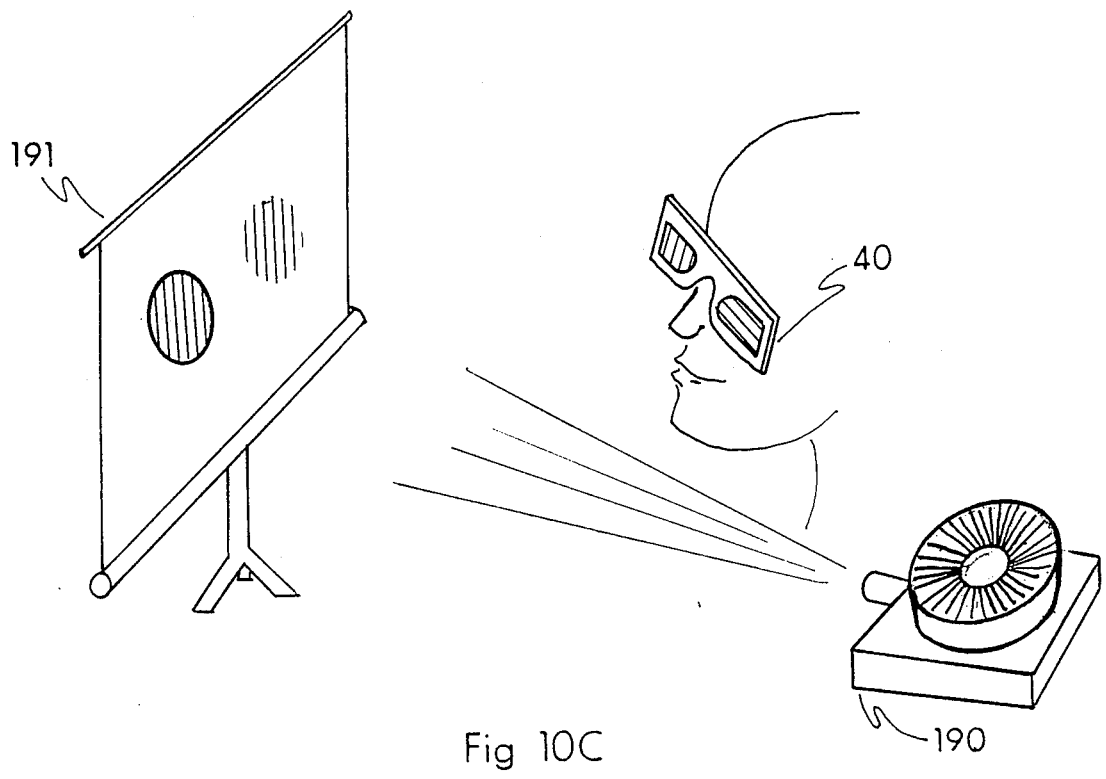

FIG. 10C shows the stimulus elements being projected upon a screen 191 so that they may be viewed. The projection device 190 can be a film-transparency projector, an opaque projector, a video-image projector, or a laser projection device. Again, the images thus projected can be still-frame or can be in motion.

Given the diverse displays which are possible, for simplicity, the phrase "presented to the observer" should be understood to comprise any suitable method for presenting two images stereoscopically to a human (or other animal) who views the images.

Alternative Viewing Devices

An essential precondition for producing the perceptual effects is the use of viewing conditions which provide the two eyes with different images. Various methods will serve this purpose, e.g.

a. constructing an image using colors, and then using colored filters to restrict what can be seen by each eye, b. presenting each eye with separate images using a stereo
scope or similar device, and c. projecting two images upon a screen using polarized light, and then using polarized filters to restrict what can be seen by each eye. The use of colored filters has been illustrated in FIGS. 2-8 and in FIG. 10. Additional consideration of the other two methods will now be presented.

Binocular Field Effects Using A Stereoscope—FIG. 11

Figure 11A:
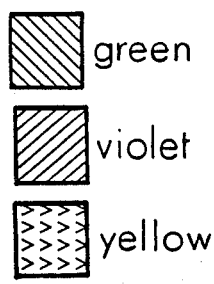
FIG. 11 (A & B) illustrates the production of luster by viewing a stimulus configuration with a stereoscope.
Figure 11A:
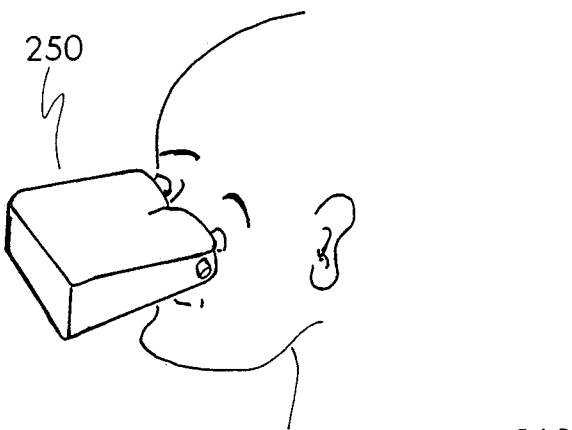
Figure 11B:
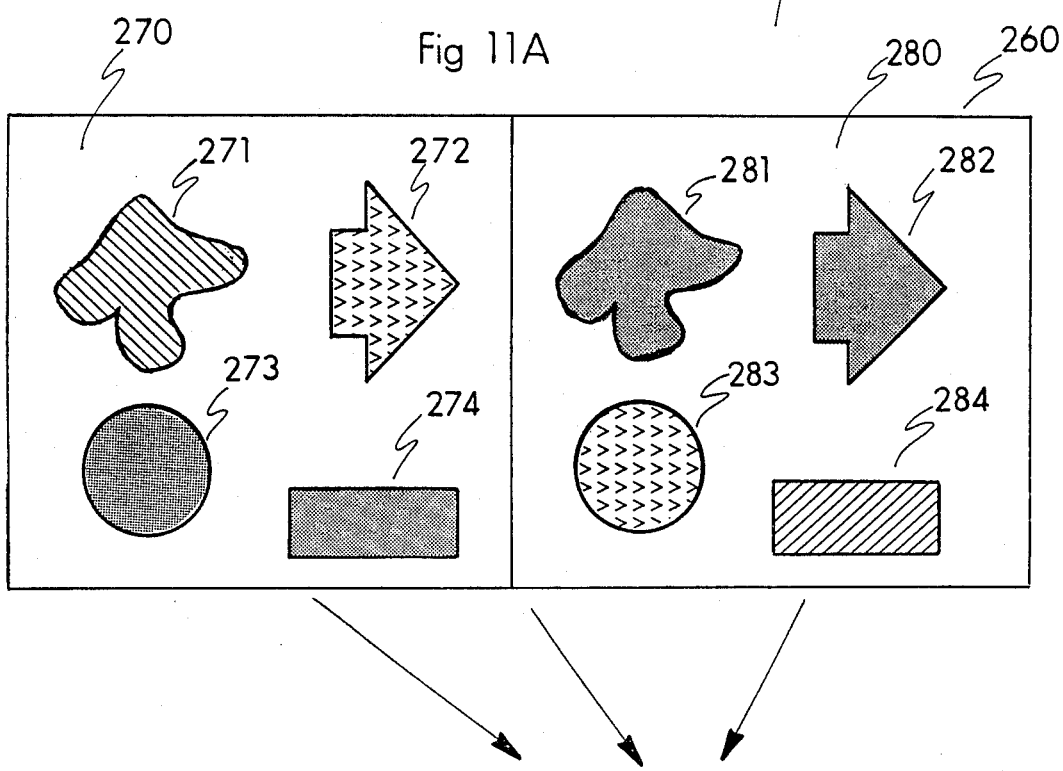
Figure 11B:
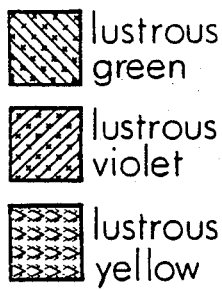
Figure 11B:
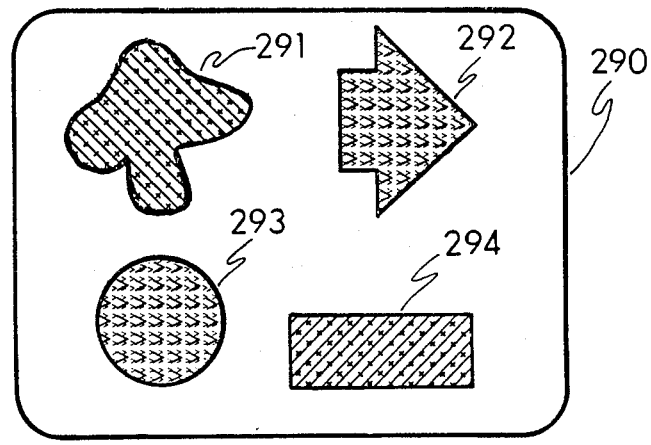

The stimulus elements can be presented to the two eyes using a stereoscope 250, as shown in FIG. 11A. With such a device, one would provide the stimulus elements to the two eyes using a special slide, represented in FIG. 11B by stereoslide 260. The left side 270 contains stimulus set 271-274, a collection of four shapes, specifically: green mushroom 271, yellow arrow 272, black circle 273, and black rectangle 274. The right side 280 contains stimulus set 281-284, a corresponding collection of four shapes, specifically: black mushroom 281, black arrow 282, yellow circle 283, and green rectangle 284. Each colored shape on the left or right has a corresponding black shape on the opposite side of the slide.

When stereoslide 260 is viewed in stereoscope 250, stimulus set 271-274 is seen as an image in the left eye, and stimulus set 281-284 forms an image in the right eye. Therefore, for each colored shape which is seen by the left eye, there is a matching black shape (at that same location in the field of view) which is seen by the right eye. Similarly, the colored shapes which are seen by the right eye have a black pair-mate which is presented to the left eye at the corresponding site. A person of normal binocular vision will synthesize the information from the two eyes, and will see binocular field 290, containing perceived shapes 291-294. In the illustration shown in FIG. 11B, all the shapes will be seen as having luster.

Using the stereoscope, one has greater latitude in the selection of colors. When using colored filters to produce the perceptual effects (glasses 40 of FIG. 2), it is necessary to use specific colors for the stimulus elements which match the filtration properties of the glasses. This is not necessary with the stereoscope; any color can be used, such as the green, violet, and yellow shown in stereoslide 260.

The stereoscopic display can be still-frame, or moving. The device for producing the stereoscopic display can use any of the methods described above, including video or other electronic imaging system.

Figure 12:
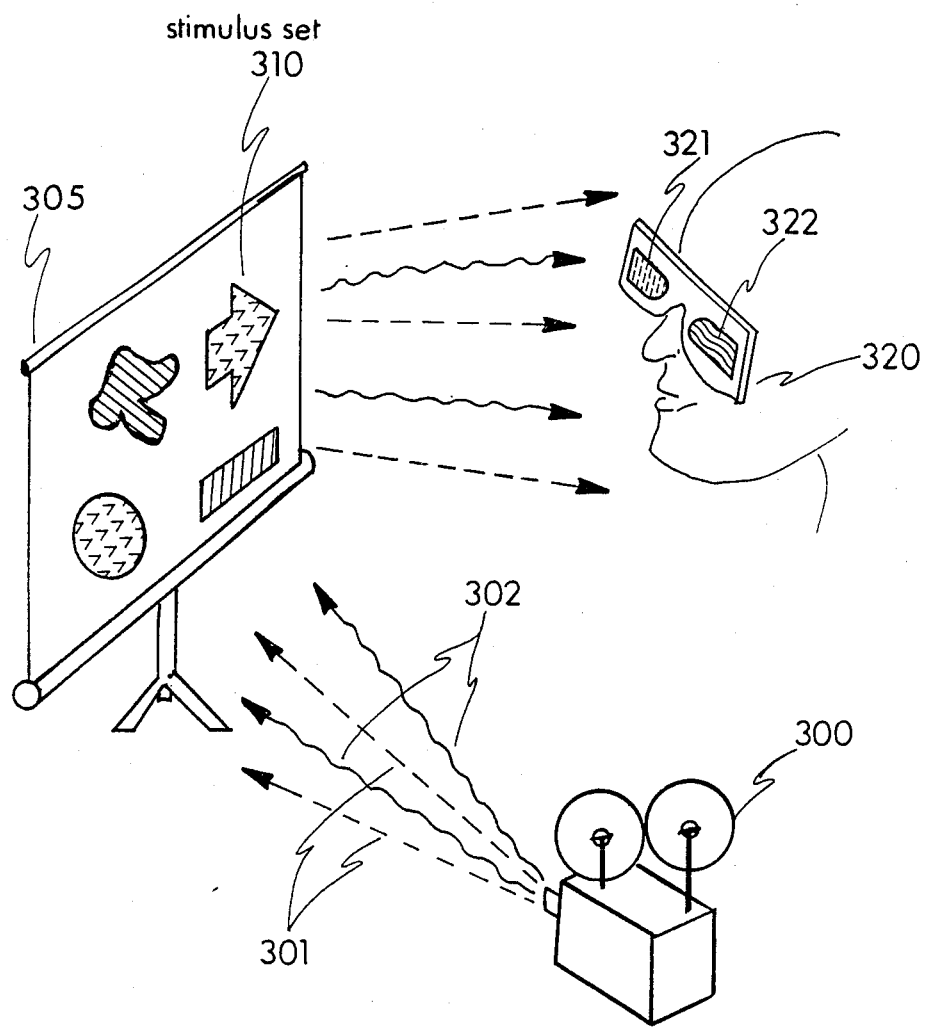
FIG. 12 illustrates the use of polarized light to produce the perception of luster.

Binocular Field Effects Using Polarized Light—FIG. 12

FIG. 12 illustrates a method for producing binocular field effects using polarized light projection and polarized filters as a device for sorting the image components to the respective eyes. Projector 300 makes use of prior art methods for projecting two images upon a screen using light with two kinds of polarity. Light polarities 301 and 302 are indicated by wavy and broken lines. Stimulus elements (contained in a stereoslide or as pair-frames on movie film) are projected upon a viewing surface 305, and the result of that projection can be seen as stimulus set 310.

The polarity of the light is preserved as it is reflected from viewing surface 305, and is selectively filtered by polarized glasses 320 being worn by the viewer. Glasses 320 use lens filters which are of different polarity—i.e. lens 321 allows polarized light 301 to pass through, but not polarized light 302, and vice versa for lens 322. Thus glasses 320 resegregate the stimulus material to reflect what was contained by the paired-frames being projected. The effect is the same as if a stereoscope were being used, and this method of display has the additional latitude for color selection described above.

It should be noted that the perceptual phenomenon being described here is not the same as the standard depth effect produced in "3-D" movies. The standard depth enhancement depends on the creation of binocular disparity in two images -slight misalignment of the edges of the stimulus elements. While the binocular field effects being described in this application produce some enhancement of depth, it is a separate and independent phenomenon. The perceptual effects described according to my invention do not require any binocular disparity.

Applications

Commercial uses for the invention include the creation of special effects in various forms of entertainment and advertising. Also, the mere demonstration of the perceptual phenomena will be of importance for research and instruction, and thus the design of the materials for these purposes should be included in a discussion of utility. An important benefit may be provided in the testing of patients being evaluated for binocular dysfunction. While the particulars for application may include a wide variety of uses, I will focus on the testing of visual dysfunction, and special effects for entertainment.

Figure 13:
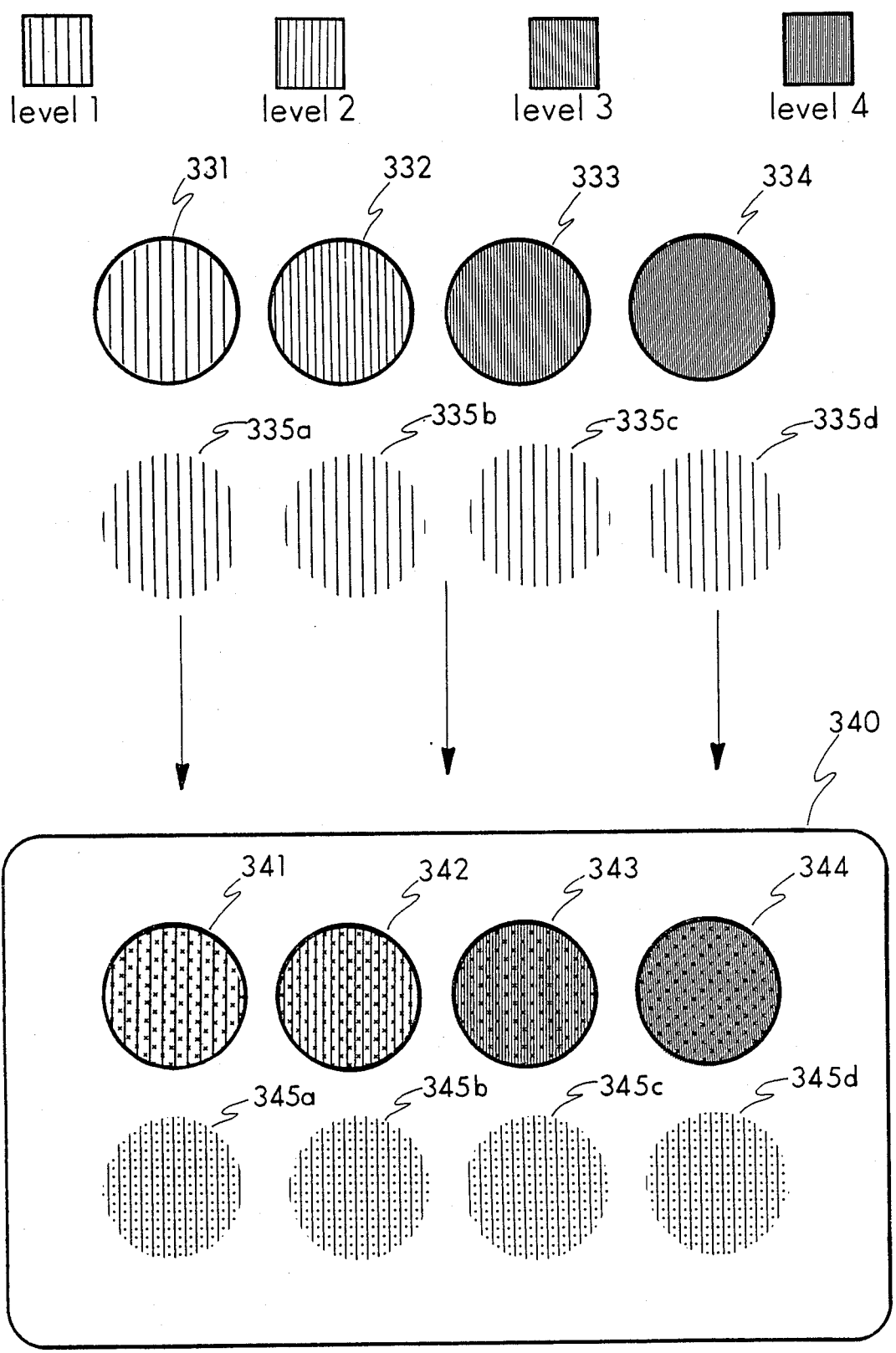
FIG. 13 shows the design of a stimulus collection which can test the strength of binocular field effect in vision.

Strength of Binocular Field Effect—FIG. 13

There are various ways in which defective binocular vision might be tested. One method is to systematically vary the amount of light which is delivered from the zone contained by the dark border. A graded sequence of stimuli can be used, as illustrated in FIG. 13, which shows a collection of disks 331–335d, as they would be designed for viewing through red-blue glasses 40 (FIG. 2).

The disks can be printed, painted, or otherwise constructed so that the disks without a rim are all the same color-brightness. The upper set of disks (which have a rim) are a graded sequence of brightness levels. Disk 331 is the same brightness as all four unrimmed disks 335a–335d. Disks 332, 333, and 334 are progressively less bright, but are the exact same color hue as all the other disks. One method of creating this stimulus collection is to use multiple layers of a color film, so the amount of light reflected or transmitted from the stimulus surface is determined by the number of layers of film. With this method, disk 331 might be created by a single film layer, 332 using two layers, etc.

When stimulus array 331–335d is viewed using glasses 40 (FIG. 2), one sees binocular perception 340, consisting of the corresponding perceived disks 341–345d. Disks 345a–345d are seen as being dark, and having a ruddy-red color. The upper set of four disks are seen as having luster, but the amount of brightness enhancement is offset proportional to the initial brightness of the stimulus. One disk among the perceived set will be seen as most equal to the lower comparison disk. In this illustration, perceived disk 343 is seen as most equal for a person of normal vision. A person with weak binocular field effect will select disk 341 or 342 as being equivalent to the lower comparison disk, depending on the degree of dysfunction. An individual with abnormally strong binocular field strength would select disk 344.

It should be clear that the four levels of brightness used in FIG. 13 are for purposes of illustration. Any practical visual test should have more brightness steps to provide better measurment of the strength of binocular field effects.

Practical Considerations

When using color filters as a means of segregating the visual images, it is essential that the colors of the image be well balanced in relation to the filters being used for viewing. In the case of enhanced brightness, the effect will be diminished substantially if the eye which perceives the boundary is able to see a difference in shading between the interior of the form and the background. The overall effect may be lost where the color used to create the stimuli has not been carefully selected with regard to the glasses. The best field effects are seen if the colored zone is virtually invisible when viewed through one of the glasses, and looks quite dark when viewed through the other. For some applications, "process printing," mixing four preselected colors in various proportions, can be used with success. However, there is always the risk that the color will involve a mix which diminishes the effect. Thus, where the stimulus material is to be printed, the best results are achieved by the use of "direct printing" methods, where one selects the exact colors of ink to be used.

A graded set of masks can be used to control the brightness of the stimulus array. The disks could be made using the same color color brightness for all the stimulus elements, and then the rimmed disks can be overlayed with a 0%, 20%, 40% or 80% mask. The dark mask serves as a counterbalance to the enhancement of brightness created by the rim (i.e. luster), and one of the masked stimuli will appear most like the dark comparison disk which has no rim.

Because of the color-balance discussed above, it is essential that the mask be color neutral. While the ink used for press-on density gradients is nominally black, in fact it may have enough hue of its own to modify perception of the color in that zone. In such a case none of the masked stimuli look quite like the comparison member.

Figure 14A:
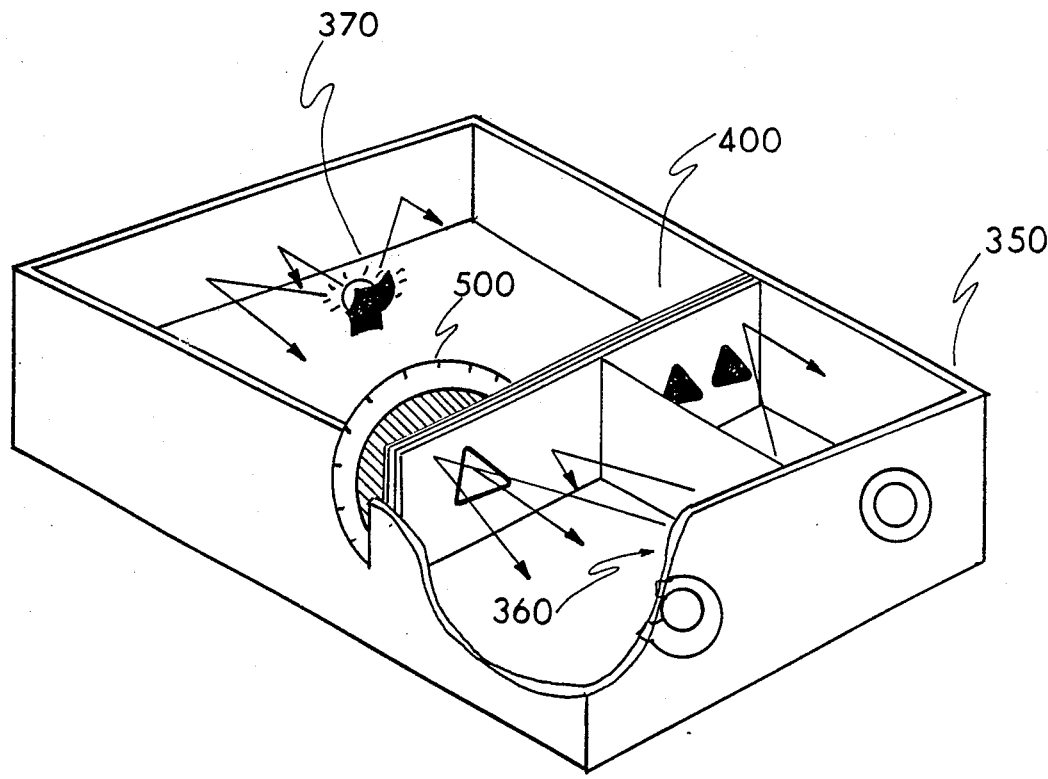
FIG. 14 shows design and components of a stereo viewer which can be used to test the strength of binocular field effects.
Figure 14B:
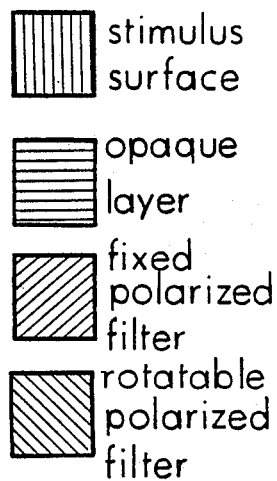
Figure 14B:
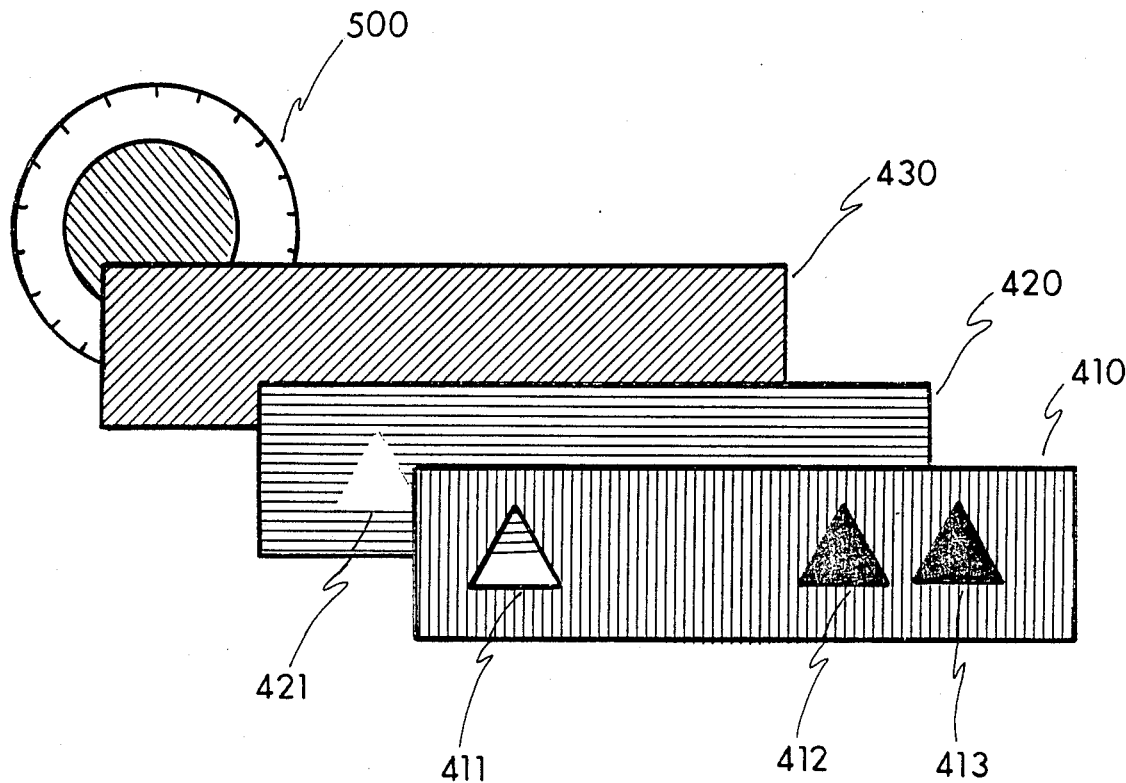

Device to Scale Luster—FIG. 14 it would be desirable to get a better measure of the strength of the field effects. A stereoscopic device can be constructed which allows systematic variation of the amount of light being delivered from the zone contained by the dark boundary, and thus can provide any degree of measurement precision which may suit the need.

One such device is a specially constructed stereo viewer, shown as 350 in FIG. 14A. The viewer uses special slides which presents stimulus forms which may vary in size, shape, thickness of dark boundary, and other factors which may be of significance in relation to the strength of binocular field effect. Composite slide 400 is one such slide; it is shown in position for viewing within device 350, and the components of the slide are shown separately in FIG. 14B.

The slide composite is designed to allow adjustment of the amount of light which is delivered from the zone contained by the boundary. By varying the amount of light shown in that zone, one can counterbalance the effect of the boundary in inducing luster, and so can arrive at a measurement of the strength of the binocular field influence for any given observer.

As shown in FIG. 14A, the device uses reflected light to illuminate the face of the slide. The light source is indicated (but not shown) at 360. At the viewing plane of the device, composite slide 400 is used for presentation of the visual stimuli.

Key elements for control of luminance are shown in FIG. 14B. The front layer 410 of composite slide 400 has a white surface which is seen as a background to the forms which are printed, painted or otherwise constructed upon the surface. A hole 411 is cut to remove the area contained by the perimeter line, so that the slide now can serve as a mask to selectively allow the transmission of light from the rear of the device, provided by light source 370, wherein the light can pass only through the zone contained by the perimeter.

The stimulus slide must be coated or laminated on the back side with a completely opaque layer to prevent the transmission of light at other sites, this layer being shown at 420 in Fig 14B, with the corresponding hole at 421. A polarized light filter 430 is bonded to each of the stimulus slides, or can be mounted as a separate component in the device. It is important that the components of the slide be relatively thin, and sandwiched tightly to prevent the perception of a depth differential between the background surface and the light transmitting surface which is formed by the holes. Proper diffusion and angling of light also will be essential in this respect.

Control of the amount of transmitted light is accomplished by the positioning of two polarizing filters—filter 430, shown in FIG. 14B, and filter 500, shown in FIG. 14A and 14B. The relative angular position of filters 430 and 500 determines the amount of light which can pass. Filter 500 is designed so that is can be rotated, thus changing the angular position between the filters, and controlling the amount of light which passes through them.

As has been previously discussed, the color balance can be critical to the perception and comparison being required. Adjustment of these factors can be accomplished by careful selection of component materials, color adjustment of the light sources, or the use of a restricted range of wavelengths (so called monochromatic light), for making the tests.

An alternative method would be to adjust the electrical power being delivered to the light source, and measure the amount of current needed to achieve a match of brightness (or other field strength comparison). Again, color balance becomes an issue since the spectral properties of the source will change at different current loads.

A major advantage of the device shown in FIG. 14 is relative simplicity. One can interchange the composite slides and vary all the stimulus parameters described above—perimeter thickness, size of form, etc. The cut-out design allows automatic adjustment for the size and shape of the form. After testing the patient by adjusting the light being delivered to one eye, the device can be turned over to evaluate the other monocular system. However, for the most critical work it would be advisable to use transmitted light for the background as well as the foreground, with multiple-masks and appropriate optics for synthesizing the components for viewing. Additionally, an advanced system should allow adjustment of background illumination as well as the light being delivered from the comparison stimulus. With either approach the illumination must be even.

Special Effects

The methods described in this application can be used to create special perceptual effects in visual material which can be presented in diverse ways. FIGS. 10, 11, and 12 show several applications of the invention, but are inadequate to show the impact of these special effects upon perception. Creation of a color luster is especially interesting -- the color has a ghost-like luminescent quality, and appears to float slightly above the viewing surface. This can be used in motion pictures, television, or books (FIGS. 10a-c) to produce a dazzling array of surrealistic effects which would be suitable for science fiction and fantasy entertainment. The effects could be used for children's cartoon shows, where the special glasses could become part of the fun. In any medium where visual images can be presented, there is the potential for producing special effects which can serve to entertain, inform, or provide additional influence of attention.

Ramifications, Scope, and Summary

Thus it is seen that, according to the invention I have provided an useful analysis of essential devices and stimulus design for producing these perceptual effects. The devices which serve this purpose include:

a. presenting separate images using a stereoscope or similar device, b. projecting two images upon a screen using polarized light, and then using polarized filters to restrict what can be seen by each eye, and c. constructing an image using colors, and then using colored filters to restrict what can be seen by each eye.

With respect to stimulus design, I have described the configurations which create the binocular field effects. Stated in the most general terms, it is necessary for one eye to perceive light or light-patterns in a zone of the visual field, and to perceive a dark boundary surrounding that zone. The other eye cannot perceive the light or light-pattern in the correponding zone, nor the presence of a dark boundary to that zone. When these conditions are met, the eye which perceives the boundary will dominate binocular perception, and the person perceives the stimulus material which is contained by the boundary rather than the visual stimulus provided at that location by the other eye.

The reader will see that I have given explicit information as to the devices and stimulus configurations which are needed for producing binocular field effects, and this is the first valid description of the means for producing these effects. Indeed, the existence of extended (nonlocal) control of brightness and contour perception was not known prior to my own disclosure of this phenomenon in my monoagraph ("Form Light, Form Bright," op cit.)

While the foregoing description contains many specifies, these should not be construed as limitations on the scope of the invention, but rather as exemplifications of several preferred embodiments. Other ramifications will occur to those skilled in the art. Accordingly, the scope of the invention should be determined by the appended claims and their legal equivalents.

What is claimed is:

1. An arrangement of viewing conditions and a configuration of visual stimulus elements for presentation to and for controlling the perceptions of a binocular observer, comprising:
    (a) means for presenting separate visual images to the respective eyes of said observer, each of said visual images being formed by a collection of elements,
    (b) means for controlling the color and brightness of said elements,
    (c) said means for presenting and said means for controlling further providing one of said eyes with a set of black elements that surround and contain a zone of the images presented to said one eye, thus forming a black border around said zone of said image, without providing such black border around the corresponding zone in the image presented to the other of said eyes, such that the portion of the image in said zone contained by said black border will dominate perception across the corresponding zone of said observer's binocular perception, and will have uniformity of dominance across said perceptual zone.

2. The arrangement of claim 1 wherein said means for presenting and said means for controlling also are arranged to provide bright image elements within said image zone contained by said black border in one said eye, and black image elements in the corresponding image zone of said other eye, such that said observer's binocular perception is of a stimulus having a uniform bright, lustrous quality across said corresponding perceptual zone.

3. The arrangement of claim 1 wherein said means for presenting and said means for controlling also are arranged to provide each of said eyes with a different pattern of image elements across extended and overlapping image zones, with said black border serving to divide the image zone of one said eye into a plurality of subzones which lie inside and outside said border, such that the pattern presented to the image subzone, which lies inside said border will dominate said observer s binocular perception within the corresponding perceptual subzone, and the pattern seen by said other eye will dominate the perceptual subzone which lies outside said border.

4. The arrangement of claim 1 wherein said means for presenting visual images comprises a plurality of color filters and means for interposing such filters between said eyes and the respective images presented to said eyes.

5. The arrangement of claim 2 wherein said means for presenting visual images includes means for projecting said images upon a viewing surface using polarized light, and means for interposing polarized filters between said images and said eyes.

6. The arrangement of claim 2 wherein said means for presenting visual images comprises a stereoscope for providing said eyes with said images.

7. The arrangement of claim 1 wherein said means for controlling said color and brightness of said elements further includes means for varying the thickness of said border, and for modifying and evaluating the degree of said dominance.

8. The arrangement of claim 2 wherein said means for controlling said color and brightness of said elements further includes means for varying the position of said border in relation to the fixation point of each of said eyes, and for evaluating said uniformity of dominance.

9. The arrangement of claim 2 wherein said means for controlling said color and brightness of said elements further includes means for varying the size of said zone contained by said border, and for evaluating said uniformity of dominance.

10. The arrangement of claim 1 wherein said means for controlling said color and brightness of said elements further includes means for varying the shape of the zone contained by said border, and for evaluating said uniformity of dominance.

11. The arrangement of claim 1 wherein said means for controlling said color and brightness of said elements further includes means for providing a binocular mixture of color elements within the zone contained by said border, and for evaluating said uniformity of dominance produced by said mixture.

12. The arrangement of claim 2 wherein said means for presenting said images comprises a stereoscope for providing the respective eyes with said images, and said means for controlling said brightness comprises a plurality of polarizing filters.

13. The arrangement of claim wherein said means for presenting said visual images comprises a viewing surface having pigmentation thereon.

14. The arrangement of claim 1 wherein said means for presenting said visual images comprises a viewing surface having a lamination of materials thereon.

15. The arrangement of claim 1 wherein said means for presenting said visual images comprises a viewing surface and means for projecting images thereon.

16. The arrangement of claim 1 wherein said means for presenting said visual images comprises an electronic display device.

17. The arrangement of claim 1 wherein said means for controlling further includes a plurality of image zones, each of which is surrounded and contained by a black border, whereby dominance of perception may be produced simultaneously at a corresponding plurality of perceptual zones in one or both of said eyes.

18. Apparatus and stimulus configurations for controlling and determining the binocular perceptions of an observer, comprising:

a. means for presenting separate visual images to the respective eyes of said observer, each of said images being formed by a collection of points,
b. means for controlling the color and brightness of said points,
c. said means for presenting and said means for controlling further providing one of said images with a set of relatively black points which form a border around and thus contain a set of points which are collectively relatively nondark, with the corresponding points in the other said image being free of such a border, such that the binocular perception of said observer at that location will be dominated by said collection of nondark points which are thus contained.

19. Apparatus and stimulus configurations for controlling and determining the binocular perceptions of an observer, comprising:

a. means for presenting separate visual images to the respective eyes of said observer, each of said images being formed by a collection of points,
b. means for controlling the color and brightness of the points,
c. said means for presenting and said means for controlling further providing each of said images with a different pattern of points, only one of said images having a set of black points which form a border around a subset of its pattern of points, such that the binocular perception of said observer will consist of a combination of the images from each said eye, specifically the black border points and the pattern points which the border in fact contains, both being surrounded by the pattern of points that are present in the image of the other eye.

* * * * *

UNITED STATES PATENT AND TRADEMARK OFFICE
CERTIFICATE OF CORRECTION

PATENT NO. : 4,863,258

DATED : September 5, 1989

INVENTOR(S) : Ernest Greene

It is certified that error appears in the above-identified patent and that said Letters Patent is hereby corrected as shown below:

```
Col 4, line 50, change "160" to -- 161 --.
Col 4, line 51, change "161" to -- 162 --.
Col. 17, line 18, change "monoagraph" to -- monograph --.
Claim 5, line 1, change "claim 2" to -- claim 1 --.
Claim 6, line 1, change "claim 2" to -- claim 1 --.
Claim 8, line 1, change "claim 2" to -- claim 1 --.
Claim 9, line 1, change "claim 2" to -- claim 1 --.
Claim 12, line 1, change "claim 2" to -- claim 1 --.
Claim 13, line 1, after the word "claim" add -- 1 --.
```

Signed and Sealed this

Fourteenth Day of August, 1990

Attest:

HARRY F. MANBECK, JR.

*Attesting Officer*   *Commissioner of Patents and Trademarks*